United States Patent
Tanaka et al.

(10) Patent No.: US 11,670,949 B2
(45) Date of Patent: Jun. 6, 2023

(54) BIO-SIGNAL MEASURING DEVICE

(71) Applicant: TECHNO-COMMONS, INC., Nagano (JP)

(72) Inventors: Akio Tanaka, Himeji (JP); ChunKit Chan, Himeji (JP); Kohei Higuchi, Himeji (JP); Kazusuke Maenaka, Himeji (JP)

(73) Assignee: TECHNO-COMMONS INC., Nagano (JP)

( * ) Notice: Subject to any disclaimer, the term of this patent is extended or adjusted under 35 U.S.C. 154(b) by 938 days.

(21) Appl. No.: 16/486,742

(22) PCT Filed: Feb. 19, 2018

(86) PCT No.: PCT/JP2018/005778
§ 371 (c)(1),
(2) Date: Aug. 16, 2019

(87) PCT Pub. No.: WO2018/155386
PCT Pub. Date: Aug. 30, 2018

(65) Prior Publication Data
US 2019/0357796 A1 Nov. 28, 2019

(30) Foreign Application Priority Data

Feb. 27, 2017 (JP) .............. JP2017-035208
Feb. 27, 2017 (JP) .............. JP2017-035211
Feb. 27, 2017 (JP) .............. JP2017-035212

(51) Int. Cl.
*H02J 7/00* (2006.01)
*A61B 5/304* (2021.01)
(Continued)

(52) U.S. Cl.
CPC ............ *H02J 7/0042* (2013.01); *A61B 5/304* (2021.01); *A61B 5/369* (2021.01); *H02J 7/00* (2013.01);
(Continued)

(58) Field of Classification Search
CPC ....... A61B 5/304; A61B 5/369; A61B 5/6802; A61B 2560/0214; A61B 5/24;
(Continued)

(56) References Cited

U.S. PATENT DOCUMENTS

2016/0270717 A1* 9/2016 Luna .................. A61B 5/743
2016/0358155 A1* 12/2016 Proud ................. A44C 5/0015

FOREIGN PATENT DOCUMENTS

WO WO-2016201366 A1 * 12/2016 .......... A61N 1/0456

* cited by examiner

*Primary Examiner* — Minh D A
(74) *Attorney, Agent, or Firm* — Manabu Kanesaka

(57) ABSTRACT

A secondary battery built in a bio-signal measuring instrument (a wearable biosensor) is charged without using a dedicated charging terminal. A bio-signal measuring device includes: a battery as an internal power source and a charging circuit for the battery; electrodes which are brought into contact with the skin surface of the human body at the time of bio-signal measurement and are connected to a predetermined power feeder at the time of charging of the battery; a bio-signal processing circuit which processes bio-signals detected at the electrodes in a predetermined manner; and a bio-signal and feed power distribution device, in which the bio-signal processing circuit and the charging circuit are switchably connected to the electrodes through the bio-signal and feed power distribution device, and at the time of the charging of the battery, the electrodes are used as charging terminals.

27 Claims, 16 Drawing Sheets

(51) Int. Cl.
*A61B 5/369* (2021.01)
*A61B 5/00* (2006.01)

(52) U.S. Cl.
CPC ......... *H02J 7/00034* (2020.01); *A61B 5/6802* (2013.01)

(58) Field of Classification Search
CPC .... A61B 5/316; A61B 2560/0209; H02J 7/00; H02J 7/0047; H02J 7/0042; H02J 2310/23; H02J 7/00034; H02J 7/0068
See application file for complete search history.

FIG.16
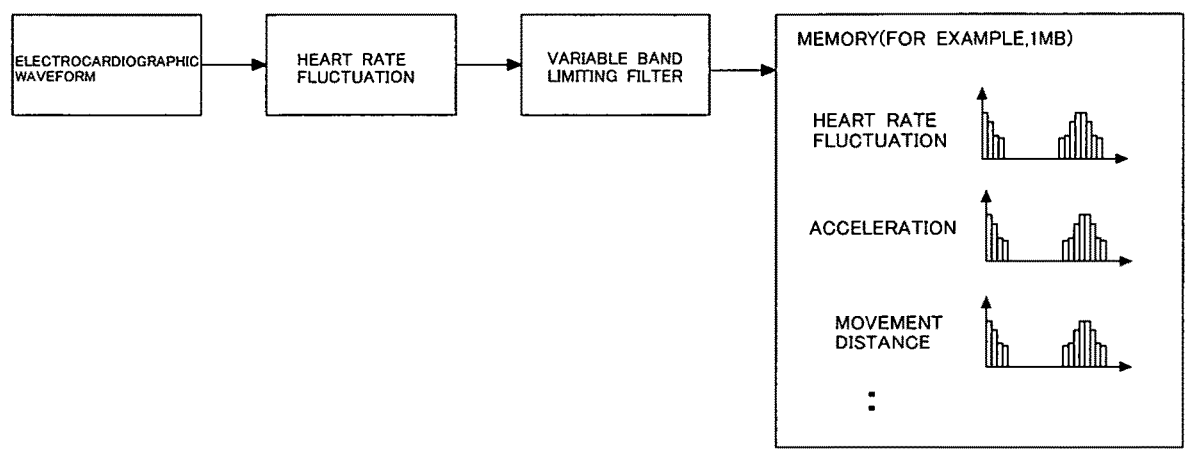
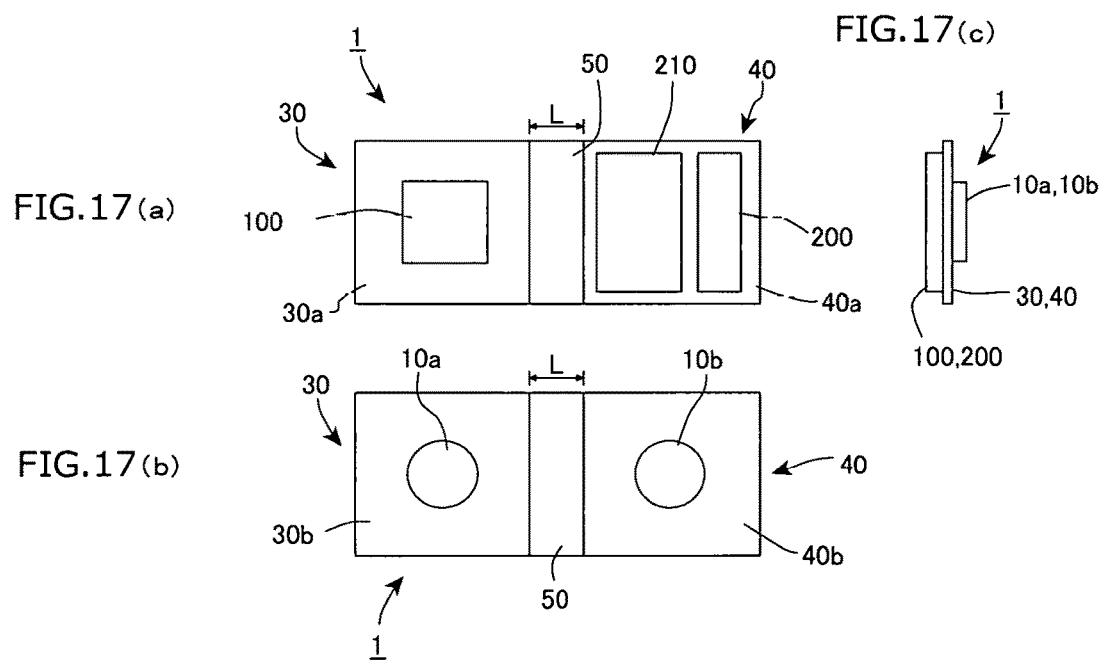

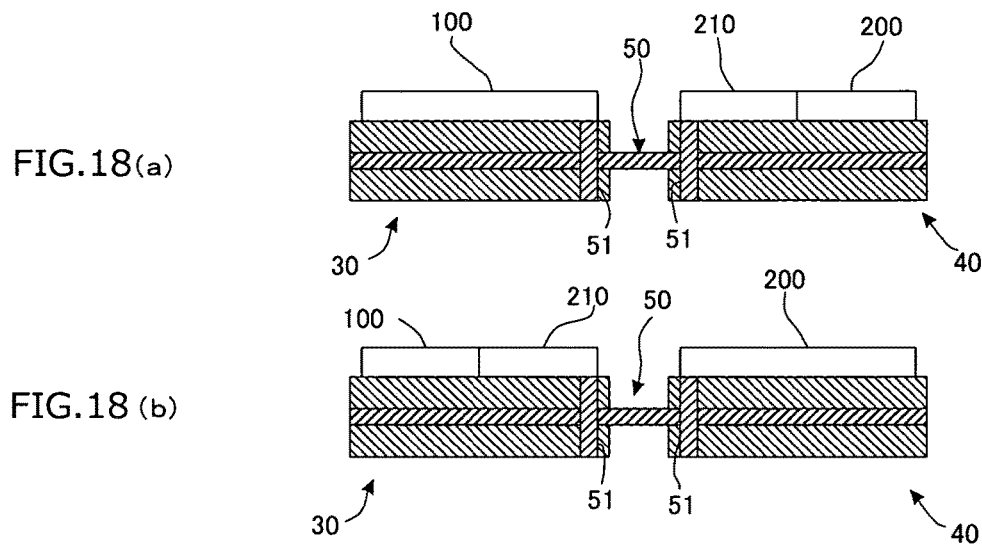
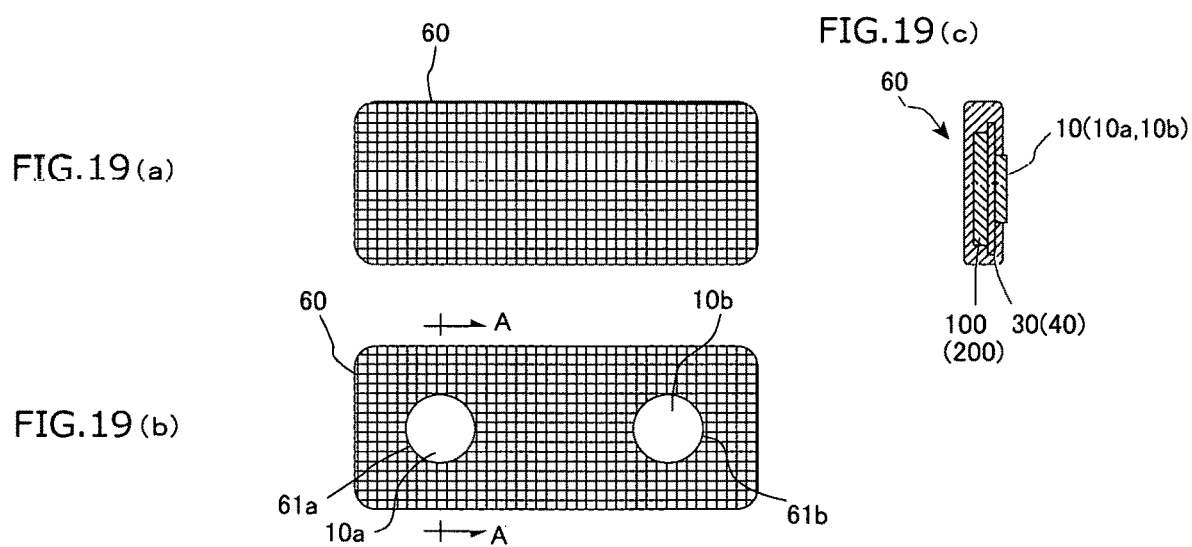

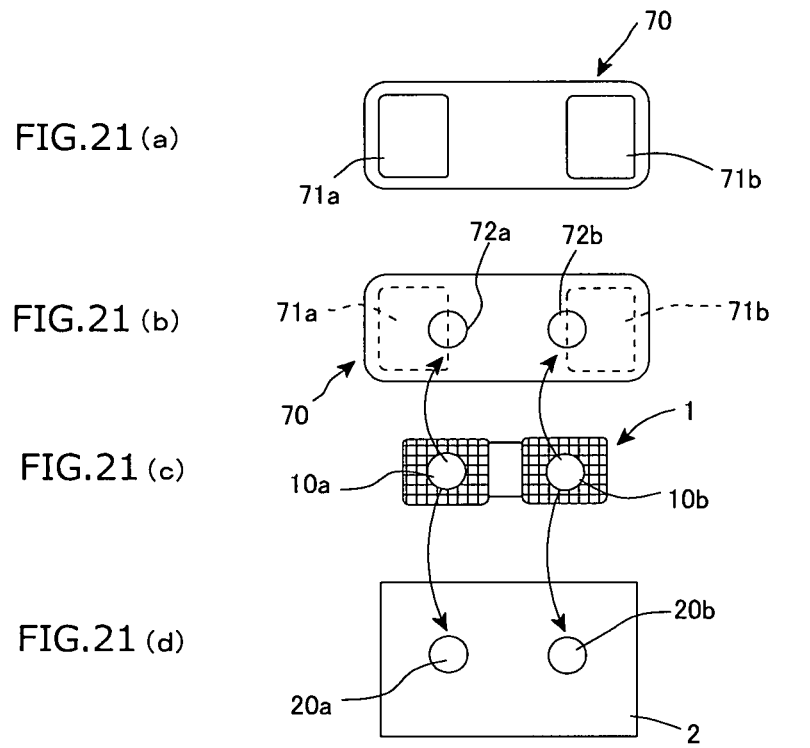
FIG.21(a)
FIG.21(b)
FIG.21(c)
FIG.21(d)
FIG.22
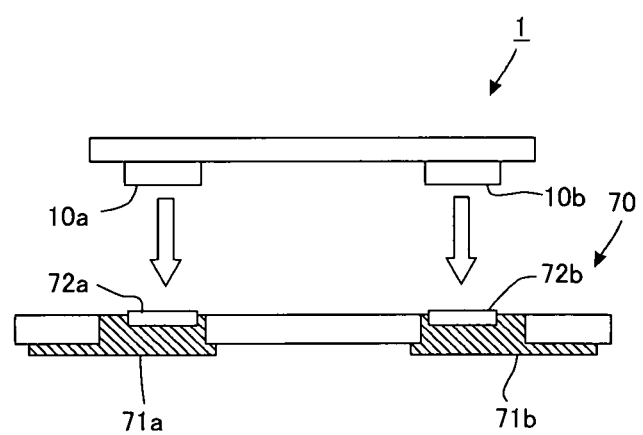

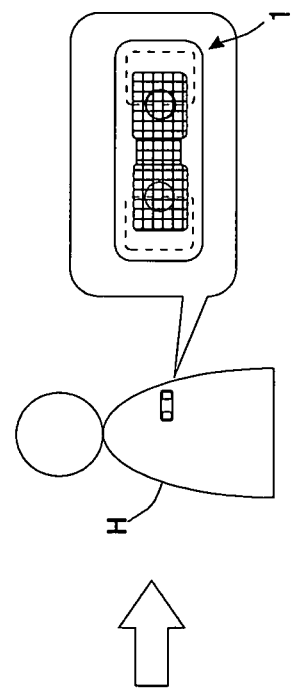
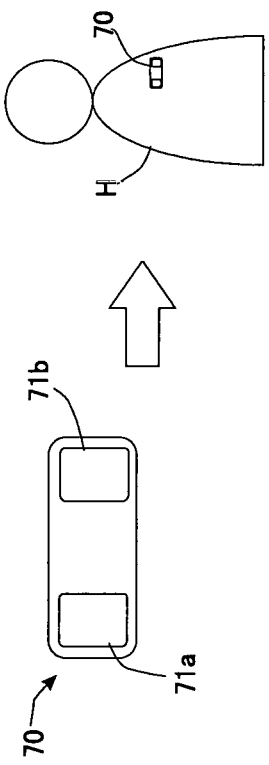
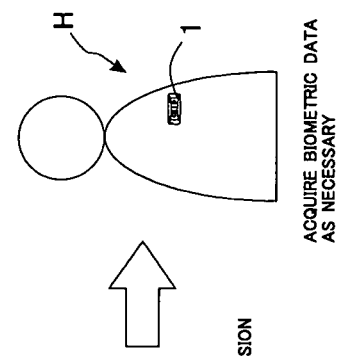
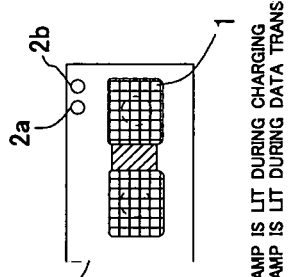
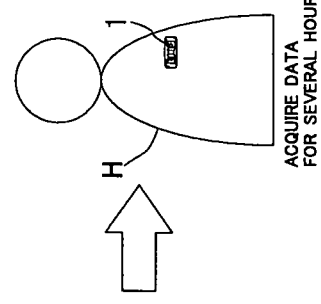

BIO-SIGNAL MEASURING DEVICE

RELATED APPLICATIONS

The present application is National Phase of International Application No. PCT/JP2018/005778 filed Feb. 19, 2018, and claims priority from Japanese Applications No. 2017-035208 filed Feb. 27, 2017, No. 2017-035211 filed Feb. 27, 2017; and No. 2017-035212 filed Feb. 27, 2017, the disclosure of which is hereby incorporated by reference herein in its entirety.

TECHNICAL FIELD

The present invention relates to a bio-signal measuring device and more specifically, to a bio-signal measuring device which includes a bio-signal measuring instrument (wearable biosensor) which is used in a state of being stuck to a living body (human body), like a sticking plaster, and a power feeder which charges a built-in battery.

BACKGROUND ART

In a wearable type bio-signal measuring instrument, in addition to a bio-signal measuring and processing unit that measures and processes, for example, an electrocardiographic signal, a myoelectric signal, an electroencephalographic signal, or the like, a battery as an internal power source that supplies a power source to the bio-signal measuring and processing unit is built in.

Usually, a secondary battery such as a lithium ion battery is used for the battery, and therefore, an SD terminal or a dedicated charging terminal for charging the secondary battery is provided, and when charging the secondary battery, a power feed terminal of a power feeder is connected to the charging terminal to charge the secondary battery (refer to, for example, PTL 1).

However, in order to provide a durable charging terminal on a small circuit substrate manufactured for a wearable instrument, it is necessary to increase the strength of the circuit substrate, and this becomes a hindrance to a reduction in size, a reduction in weight, a reduction in thickness, or flexibility.

Further, for example, in order to enable measurement even during bathing, the entire sensor needs to have a waterproof structure. However, in order to provide waterproof measures to the charging terminal such as an SD terminal, a considerable devisal is required, and a structure becomes complicated, which causes an increase in cost.

Further, in some models, wireless communication means (for example, Bluetooth (registered trademark) or the like) is incorporated in a bio-signal measuring instrument, and the measured bio-signal is transmitted in real time to external equipment such as a portable terminal. However, there is a problem such as a narrow communication range or severe battery consumption.

Therefore, in many cases, the measured bio-signal is stored in a built-in memory, a bio-signal measuring instrument is detached from the human body and connected to a personal computer or a portable terminal to collect the bio-signal from the built-in memory.

However, it is inefficient and undesirable to separately perform the collection of the bio-signal and the charging of the secondary battery.

Further, an operating power source (drive power source) is supplied from the secondary battery to the bio-signal measuring and processing unit or the like. However, in order to reduce the consumption of the secondary battery as much as possible, it is preferable to supply the operating power source to the bio-signal measuring and processing unit or the like only when the bio-signal measuring instrument is actually mounted to the human body.

CITATION LIST

Patent Literature

[PTL 1] Japanese Unexamined Patent Application Publication No. 2015-163225

SUMMARY OF INVENTION

Technical Problem

Therefore, a first object of the present invention is to enable charging of a secondary battery built in a bio-signal measuring instrument (wearable biosensor) without using a dedicated charging terminal. Further, the object of the present invention is to provide a bio-signal measuring instrument which is compact and thin and can be mounted to a living body almost without discomfort.

Further, a second object of the present invention is to make it possible to collect a bio-signal through a power feeder which is used in charging, at the time of charging of a secondary battery built in the bio-signal measuring instrument.

Further, a third object of the present invention is to reduce consumption of a battery built in a bio-signal measuring instrument (wearable biosensor) as much as possible. Further, the present invention has an object to eliminate a mechanical power source switch and enhance waterproofness.

Solution to Problem

In order to achieve the first object described above, according to a first aspect of the present invention, there is provided a bio-signal measuring device including: a bio-signal measuring instrument which is used in a state of being mounted to a living body, in which the bio-signal measuring instrument includes a battery as an internal power source and a charging circuit for the battery, a plurality of electrodes which are brought into contact with a skin surface of a human body at the time of bio-signal measurement and are connected to a predetermined power feeder at the time of charging of the battery, a bio-signal processing circuit which processes bio-signals detected at the electrodes in a predetermined manner, and bio-signal and feed power distribution means, the bio-signal processing circuit and the charging circuit are switchably connected to the electrodes through the bio-signal and feed power distribution means, at the time of the bio-signal measurement, the bio-signals detected at the electrodes are supplied to the bio-signal processing circuit through the bio-signal and feed power distribution means, and at the time of the charging of the battery, feed power which is supplied from the power feeder is supplied to the charging circuit through the bio-signal and feed power distribution means.

In the first aspect of the present invention, the bio-signal and feed power distribution means includes a signal transfer circuit and a power transfer circuit, the signal transfer circuit leads the bio-signal to the bio-signal processing circuit at the time of the bio-signal measurement and blocks a flow of the feed power to the bio-signal processing circuit at the time of the charging of the battery, and the power transfer circuit leads the feed power to the charging circuit at the time of the charging of the battery and blocks a flow of the bio-signal to the charging circuit at the time of the bio-signal measurement.

In a case where the feed power which is supplied from the power feeder is a direct current, preferably, a DC cut filter is used for the signal transfer circuit and a non-linear circuit which includes a diode or a transistor is used for the power transfer circuit.

Further, in a case where the feed power which is supplied from the power feeder is an alternating current, preferably, a low-pass filter is used for the signal transfer circuit and a high-pass filter and a rectifying circuit are used for the power transfer circuit.

As another aspect of the first aspect of the present invention, an on/off switch circuit may be used for the power transfer circuit.

A reed switch which is controlled by magnetism of magnetism generating means provided on the power feeder side can be used for the switch circuit.

Further, as another aspect, a semiconductor switch which is turned on and off according to a voltage between the electrodes or impedance between the electrodes may be used for the switch circuit.

Further, as another aspect, a two-contact switching circuit having a first contact which connects the electrodes to the bio-signal processing circuit and a second contact which connects the electrodes to the charging circuit may be used for the bio-signal and feed power distribution means, and the first contact side may be closed at the time of the bio-signal measurement and the second contact side may be closed at the time of the charging of the battery.

A reed switch in which the first contact side is closed in a normal state may be used for the two-contact switching circuit, and in this case, at the time of the charging of the battery, the second contact side is closed by magnetism of magnetism generating means provided on the power feeder side.

As another aspect, when a voltage between the electrodes is less than a predetermined voltage value or impedance between the electrodes is equal to or more than a predetermined value, the first contact side may be closed, and when the voltage between the electrodes is equal to or more than the predetermined voltage value or the impedance between the electrodes is less than the predetermined value, the second contact side may be closed.

The bio-signal measuring device according to the first aspect of the present invention further includes a power feeder having power feed terminals which come into contact with the electrodes at the time of the charging of the battery, in which the power feeder is provided with a charging end determination circuit which terminates the charging of the battery when a current flowing to the power feed terminals is equal to or less than a predetermined value.

According to a preferred aspect of the first aspect of the present invention, the bio-signal measuring device further includes an automatic power source switch which determines that the electrodes are in contact with the living body, when a resistance value between the electrodes is equal to or less than a predetermined value, and supplies a power source of the battery to the bio-signal processing circuit.

Further, an aspect in which an electrocardiographic signal measuring and processing unit, an myoelectric signal measuring and processing unit, and an electroencephalographic signal measuring and processing unit are included in the bio-signal processing circuit and the bio-signal measuring device has a mounting state check function of operating predetermined warning means as poor mounting when any of the measured signals shows an abnormal value is also included in the first aspect of the present invention.

Further, an aspect in which the bio-signal processing circuit and the power feeder have a communication function of performing communication through the electrodes and the power feed terminals, and at the time of the charging of the battery, the bio-signal data processed in the bio-signal processing circuit is transmitted to the power feeder side is also included in the first aspect of the present invention.

At the time of the charging of the battery, a predetermined command can be provided from the power feeder to the bio-signal processing circuit.

Further, the bio-signal measuring device according to the first aspect of the present invention further includes a first substrate in which the bio-signal processing circuit is mounted on one surface; and a second substrate in which the battery and the charging circuit for the battery are mounted on one surface, in which the electrode is provided on the other surface side of each of the first substrate and the second substrate, and the first substrate and the second substrate are connected through a low-bending rigidity part having conductive wiring.

Preferably, each of the first substrate and the second substrate has a waterproof cover which has an opening portion for exposing the electrode and covers a portion other than the electrode.

As another aspect, the bio-signal measuring device may further include a waterproof cover made of a low-rigidity material, which covers the entirety of the bio-signal measuring instrument including the first substrate, the second substrate, and the low-bending rigidity part, and such an aspect is also included in the first aspect of the present invention.

Further, the bio-signal measuring device according to the first aspect of the present invention further includes an adhesive tape for mounting which is stuck to the living body prior to the bio-signal measurement, in order to improve the convenience of use, in which connection electrodes to the living body, which are made of a magnetic material, are disposed at an interval equal to an interval between the electrodes on the adhesive tape for mounting, the electrodes are made of a permanent magnet material, and the bio-signal measuring instrument is mounted to the living body through the adhesive tape by magnetic attraction of the electrodes to the connection electrodes.

In order to achieve the second object described above, according to a second aspect of the present invention, there is provided a bio-signal measuring device including: a bio-signal measuring instrument which includes a plurality of electrodes which detect a bio-signal in contact with a skin surface of a human body, a bio-signal processing circuit which processes the bio-signals detected at the electrodes in a predetermined manner and stores the processed bio-signals in a memory, a battery as an internal power source, and a charging circuit for the battery, and is used in a state of being mounted to the human body; and a power feeder which supplies predetermined charging power to the battery through the charging circuit, in which the power feeder includes communication means for transmitting the bio-signals stored in the memory to predetermined external equipment.

In the second aspect of the present invention, preferably, the communication means has a bidirectional communication function, and predetermined information which includes a biological data processing program is provided from the external equipment to the bio-signal processing circuit through the communication means.

Further, according to a preferred aspect of the second aspect of the present invention, the power feeder has power feed terminals which are detachably connected to the electrodes, and communication between the power feeder and the bio-signal measuring instrument is performed through the electrodes and the power feed terminals.

More preferably, the bio-signal measuring instrument includes a transmission unit which reads the biological data from the memory and transmits the biological data, and connection detection means for outputting a connection detection signal if the power feed terminals are connected to the electrodes, and the transmission unit transmits the biological data to the power feeder if the connection detection signal is output from the connection detection means.

Further, it is preferable that the biological data in the memory is deleted after the transmission of the biological data to the power feeder.

In order to achieve the third object described above, according to a third aspect of the present invention, there is provided a bio-signal measuring device including: a bio-signal measuring instrument which is used in a state of being mounted to a living body, the bio-signal measuring instrument including a pair of electrodes which is brought into contact with the living body at the time of bio-signal measurement, a bio-signal processing circuit which processes bio-signals detected at the electrodes in a predetermined manner, and a battery which supplies a power source to the bio-signal processing circuit; a power source start switch which turns on and off a power source which is supplied from the battery to the bio-signal processing circuit; and a control unit which controls the power source start switch, in which the control unit monitors an inter-electrode resistance existing between the electrodes, turns off the power source start switch when the inter-electrode resistance is a value exceeding a predetermined threshold value, and supplies a power source from the battery to the bio-signal processing circuit by turning on the power source start switch when the inter-electrode resistance is equal to or less than the threshold value.

In the third aspect of the present invention, as a preferred aspect, the control unit has a two-input type comparator, a power source voltage in the device is set to be V0, a voltage V1 (=R2/(R1+R2)) which is obtained by dividing the power source voltage V0 with a voltage dividing circuit which includes resistors R1 and R2 connected between an in-device power source and a ground is applied to an input terminal on one side of the comparator, a voltage V2 (=R4/(R3+R4+R5)) which is obtained by dividing the power source voltage V0 with a voltage dividing circuit which includes a resistor R3 connected between the electrode on one side and the in-device power source, a resistor R4 connected between the electrode on the other side and the ground, and an inter-electrode resistance R5 is applied to an input terminal on the other side of the comparator, the resistors R2, R3, and R4 have the same resistance value Ra, the resistor R1 has a resistance value Rb higher than the resistance value Ra, and the threshold value is defined by Rb−Ra.

In the third aspect of the present invention, it is preferable that the resistors R1 to R4 are high resistance elements having a consumption current of 1 µA or less.

Advantageous Effects of Invention

According to the first aspect of the present invention, the electrode for originally detecting a bio-signal is used as a charging terminal, whereby it is not necessary to provide a dedicated charging terminal such as an SD terminal, and the configuration of the bio-signal measuring instrument is simplified, and thus the size, the weight, and the thickness can be further reduced, and sufficient waterproof measures can be taken.

Further, a configuration, in which the bio-signal measuring device includes the first substrate in which the bio-signal processing circuit is mounted on the surface on one side thereof, and the second substrate in which the battery and the charging circuit for the battery are mounted on the surface on one side thereof, and the electrode is provided on the side of the surface on the other side of each of the first substrate and the second substrate, and the first substrate and the second substrate are connected through the low-bending rigidity part having conductive wiring, is adopted, whereby it is possible to provide a small and thin bio-signal measuring instrument which can be mounted on a living body almost without discomfort.

According to the second aspect of the present invention, the biological data stored in the memory of the bio-signal measuring instrument (sensor chip) can be transmitted to the external equipment through the power feeder even during the charging of the battery, and on the contrary, a predetermined command can be provided from the external equipment to the sensor chip through the power feeder or firmware or the like can be rewritten, and therefore, it is possible to collect effective bio-signals in order to analyze data.

According to the third aspect of the present invention, only when the bio-signal measuring instrument (wearable biosensor) is mounted to the human body, the power source start switch is turned on, so that a power source is supplied from the battery to the bio-signal processing circuit, and otherwise, the power source start switch is turned off. Therefore, battery consumption can be reduced as much as possible. Further, the power source switch is composed of a comparator and a resistance element and is not a mechanical power source switch, and therefore, it is possible to enhance waterproofness.

BRIEF DESCRIPTION OF DRAWINGS

FIG. 16 is a schematic diagram showing an example of data which is transmitted in the fifth embodiment.

FIG. 17(*a*) is a front view of the component mounting side on the bio-signal measuring instrument, FIG. 17(*b*) is a rear view on the electrode side of the bio-signal measuring instrument, and FIG. 17(*c*) is a side view of the bio-signal measuring instrument.

FIGS. 18(*a*) and 18(*b*) are schematic diagrams for describing substrate connection structures of the bio-signal measuring instrument.

FIG. 19(*a*) is a front view on the component mounting side of the bio-signal measuring instrument with the waterproof cover stuck thereto, FIG. 19(*b*) is a rear view on the electrode side of the bio-signal measuring instrument, and FIG. 19(*c*) is a sectional view taken along line A-A of FIG. 19(*b*).

FIGS. 21(*a*), 21(*b*), 21(*c*) and 21(*d*) are schematic diagrams showing the relationship between the bio-signal measuring instrument, an adhesive tape for mounting, and the power feeder.

FIG. 22 is a side view showing the bio-signal measuring instrument and the adhesive tape for mounting in a separated state.

FIGS. 23(*a*), 23(*b*), 23(*c*), 24(*d*), 24(*e*) and 24(*f*) are schematic diagrams showing examples of use state of the bio-signal measuring device according to the present invention.

DESCRIPTION OF EMBODIMENTS

Next, some embodiments of the present invention will be described with reference to the drawings. However, the present invention is not limited thereto.

Figure 1:
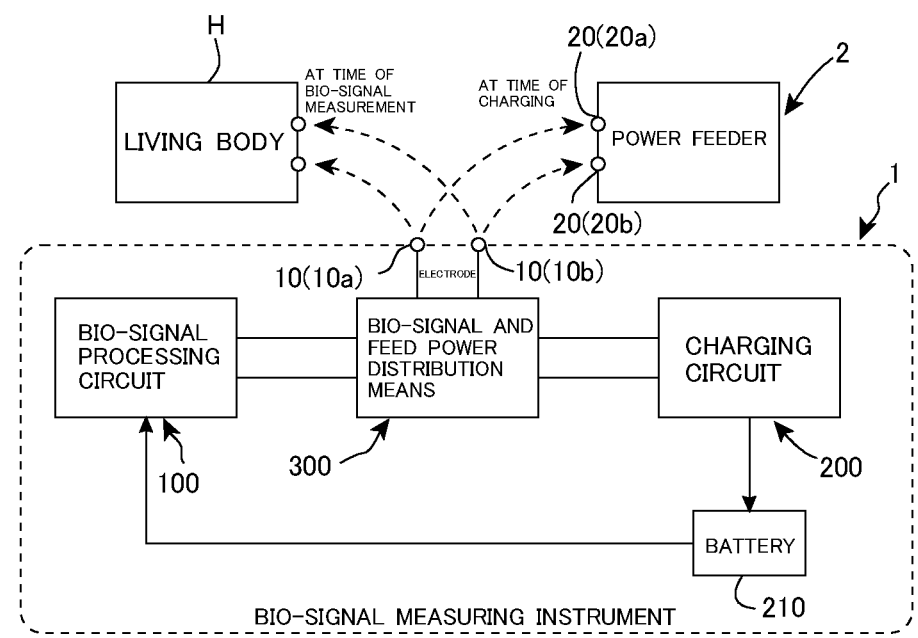
FIG. 1 is a schematic diagram showing a first embodiment of a bio-signal measuring device according to the present invention.

As shown in FIG. 1, a bio-signal measuring device according to this embodiment (a first embodiment) includes a bio-signal measuring instrument 1 as a wearable biosensor (sensor chip) and a power feeder (a charger) 2 which feeds charging power to a secondary battery 210 built in the bio-signal measuring instrument 1.

The bio-signal measuring instrument 1 includes, as a basic configuration, a pair of electrodes 10a and 10b, a bio-signal processing circuit 100, the secondary battery 210 as an internal power source, a charging circuit 200 for charging the secondary battery 210, and bio-signal and feed power distribution means 300. The bio-signal processing circuit 100 and the charging circuit 200 are switchably connected to the electrodes 10a and 10b through the bio-signal and feed power distribution means 300.

The electrodes 10a and 10b are brought into contact with a living body (human body) H at the time of bio-signal measurement and brought into contact with power feed terminals 20a and 20b of the power feeder 2 at the time of charging. That is, in the present invention, the electrodes 10a and 10b are used as both bio-signal detection terminals and charging terminals and do not particularly have terminals for charging only.

In a case where it is not necessary to distinguish the electrodes 10a and 10b from each other, they are collectively referred to as an electrode 10. Similarly, in a case where it is not necessary to distinguish the power feed terminals 20a and 20b from each other, they are collectively referred to as a power feed terminal 20. The electrode 10 may include three or more electrodes.

The bio-signal processing circuit 100 processes a potential or a current such as a cardiac potential, a myoelectric potential, brain waves, or skin resistance as biological data detected at the electrode 10. As the bio-signal processing circuit 100, a differential amplifier, an A/D converter, an MCU, a memory, or the like can be used. In order to measure the skin resistance, a voltage generator or a current generator, which causes a current to flow to the living body H through the electrode 10, may be used.

The charging circuit 200 charges the secondary battery 210 (there is a case where it is simply referred to as a "battery") such as a lithium ion battery mounted on the bio-signal measuring instrument 1. The battery 210 supplies electric power to each part of the bio-signal measuring instrument 1.

The bio-signal and feed power distribution means 300 leads the bio-signal to the bio-signal processing circuit 100 at the time of the bio-signal measurement and leads the feed power from the power feeder 2 to the charging circuit 200 at the time of the charging. The bio-signal and feed power distribution means 300 has several configuration examples.

Figure 2:
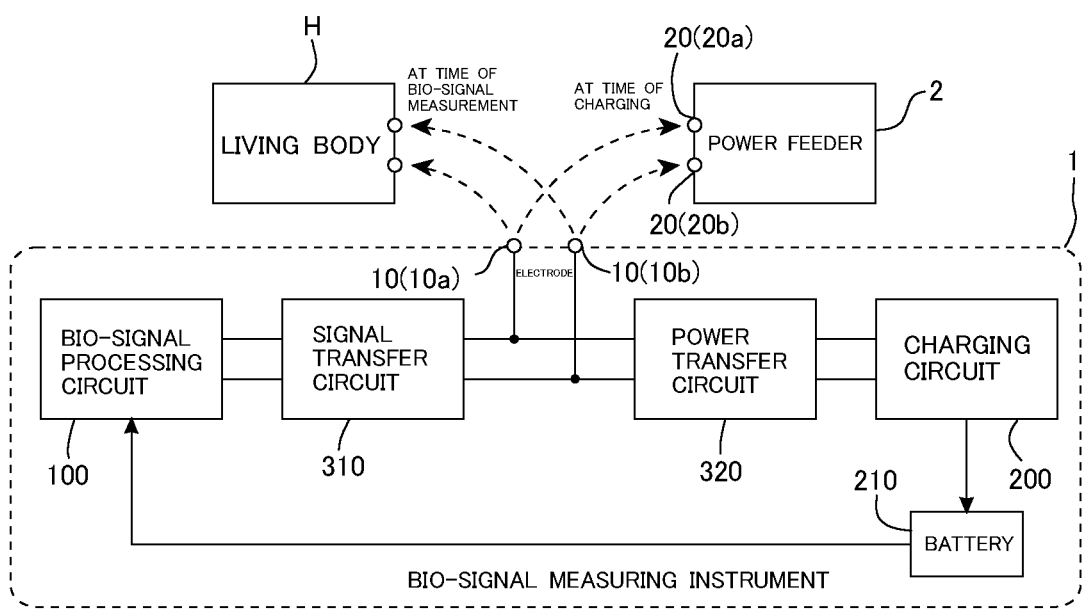
FIG. 2 is a schematic diagram showing a first example of bio-signal and feed power distribution means provided in the first embodiment.

First, in a first example shown in FIG. 2, a signal transfer circuit 310 and a power transfer circuit 320 are used for the bio-signal and feed power distribution means 300.

The signal transfer circuit 310 is connected between the electrode 10 and the bio-signal processing circuit 100, and leads the bio-signal to the bio-signal processing circuit 100 at the time of the bio-signal measurement and blocks the flow of the feed power to the bio-signal processing circuit at the time of the charging of the battery.

The power transfer circuit 320 is connected between the electrode 10 and the charging circuit 200, and leads the feed power to the charging circuit 200 at the time of the charging of the battery and blocks the flow of the bio-signal to the charging circuit 200 at the time of the bio-signal measurement.

Figure 3:
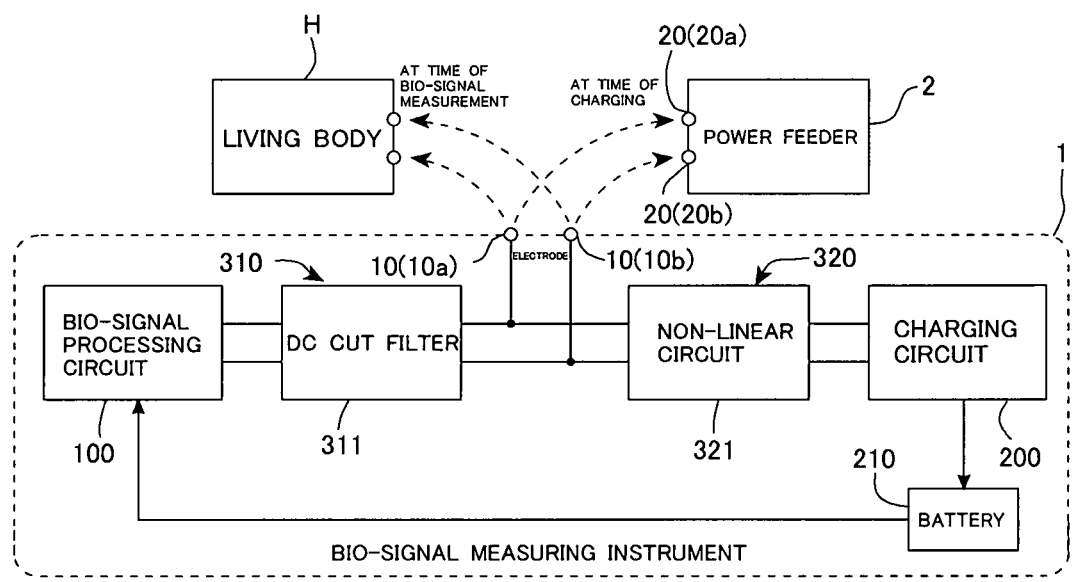
FIG. 3 is a schematic diagram showing a second example of the bio-signal and feed power distribution means.

As a second example of the bio-signal and feed power distribution means 300, in the case of DC power feed, as shown in FIG. 3, a DC cut filter 311 is used for the signal transfer circuit 310. The DC cut filter 311 allows passage of the bio-signal (alternating current) and blocks the passage of DC power. The DC cut filter 311 may be a capacitor.

Further, in the case of the DC power feed, as shown in FIG. 3, a non-linear circuit 321 is preferably adopted for the power transfer circuit 320. The non-linear circuit 321 has low impedance when power feed voltage is high voltage, and has high impedance at low voltage such as biological voltage, and functions as the power transfer circuit 320.

Figure 4A:
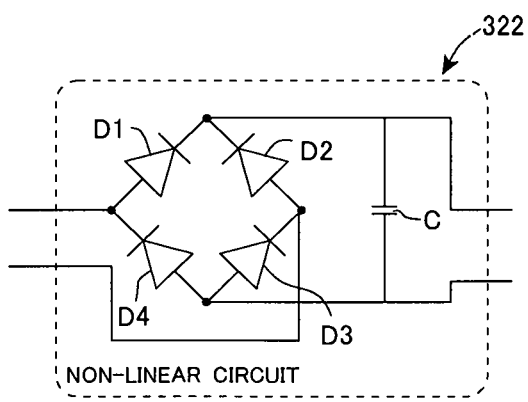
FIGS. 4(a) and 4(b) are circuit diagrams showing two specific examples of a non-linear circuit in the second example.
Figure 4B:
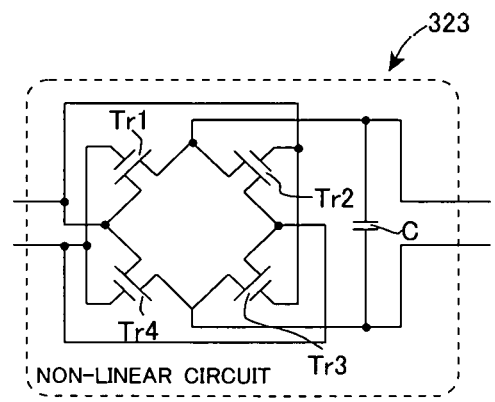

As the non-linear circuit 321, a non-linear circuit 322 having a bridge connection of four diodes D1 to D4 shown in FIG. 4(a) and a capacitor C, and a non-linear circuit 323 having a bridge connection of transistors (in this example, FETs) Tr1 to Tr4 as four semiconductor switches shown in FIG. 4(b) and a capacitor C can be exemplified.

The non-linear circuits 322 and 323 may be configured of two non-linear elements. However, a full-wave rectifying circuit is formed by forming a bridge with four non-linear elements, whereby, for example, the power feed terminal 20a is set to be a positive pole, the power feed terminal 20b is set to be a negative pole, the positive power feed terminal 20a is connected to the electrode 10a, and the negative power feed terminal 20b is connected to the electrode 10b, and conversely, even if the negative power feed terminal 20b is connected to the electrode 10a and the positive power feed terminal 20a is connected to the electrode 10b, a normal operation is made.

In a case where a diode D is used as shown in FIG. 4(a), since the rising voltage of the diode D is in a range of 0.5 to 0.7 V, the diode D is not turned on in a normal bio-signal. Therefore, there is no case where the bio-signal flows into the charging circuit 200.

Further, in a case where a transistor (FET) Tr is used as shown in FIG. 4(b), the transistor Tr can further increase an on-voltage according to a threshold value or reduce a leak current.

Although it differs according to the on-resistance or the flowing current of the diode D or the transistor Tr of the non-linear element, if a voltage which is used as the DC power feed is set to be, for example, in a range of 6 to 8 V, the output voltage of the non-linear circuits 322 and 323 is, for example, in a range of about 4.5 to 6.5 V.

Figure 5:
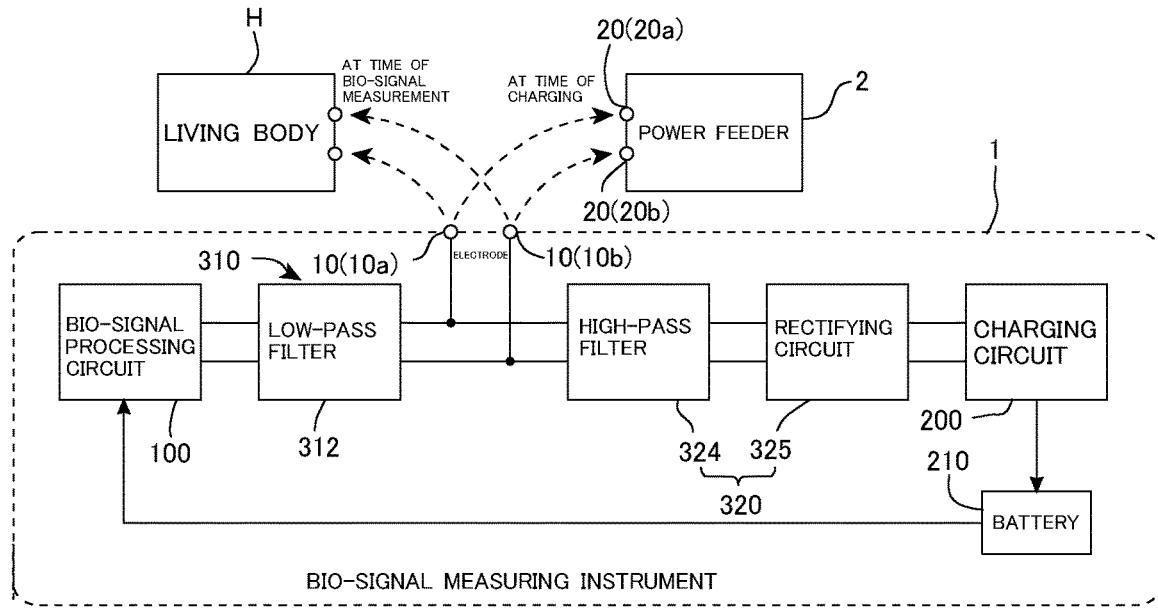
FIG. 5 is a schematic diagram showing a third example of the bio-signal and feed power distribution means.

Next, as a third example of the bio-signal and feed power distribution means 300, in the case of AC power feed, as shown in FIG. 5, a low-pass filter 312 is used for the signal transfer circuit 310, and a high-pass filter 324 and a rectifying circuit 325 are used for the power transfer circuit 320.

The low-pass filter 312 allows passage of the bio-signal. However, it blocks passage of alternating-current feed power. In contrast, the high-pass filter 324 allows the passage of the alternating-current feed power. However, it blocks the passage of the bio-signal.

It is preferable to adopt a differential configuration (balanced drive) as the AC power feed. The reason is because, if a single-ended configuration (unbalanced drive) is used for the two electrodes 10a and 10b having high impedance, the GND (ground) potential of the bio-signal measuring instrument 1 becomes unstable, and if the GND is touched, there is a case where the output voltage of the rectifying circuit 325 changes.

The frequency component of the bio-signal is present in a range of around 0.01 Hz to several kHz. The frequency which is used for the AC power feed is set to, for example, 13.56 MHz (Industry-Science-Medical band), whereby it can be separated from the bio-signal by about four digits, and thus the low-pass filter 312 can be used effectively.

Further, the cutoff frequency of the low-pass filter 312 is set to a range of several kHz to several tens of kHz, whereby the feed power can be attenuated by about −40 dB even in a primary filter, and therefore, sufficient blocking performance of the feed power can be obtained.

The non-linear circuits 322 and 323 shown in FIGS. 4(a) and 4(b) may be used for the rectifying circuit 325.

Figure 6:
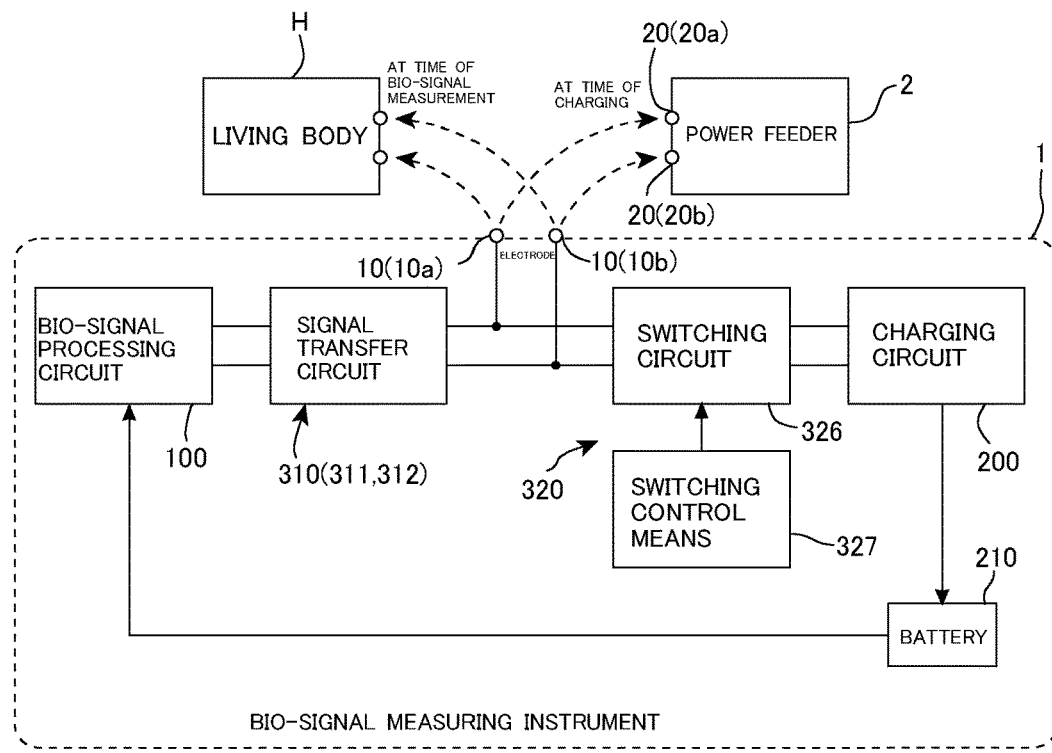
FIG. 6 is a schematic diagram showing a fourth example of the bio-signal and feed power distribution means.

As a fourth example of the bio-signal and feed power distribution means 300, as shown in FIG. 6, a switching circuit 326 can also be used for the power transfer circuit 320. The switching circuit 326 here is a switching circuit which is turned on and off by switching control means 327, and switches shown in FIGS. 7(a) to 7(c) can be exemplified for the switching circuit.

Figure 7A:
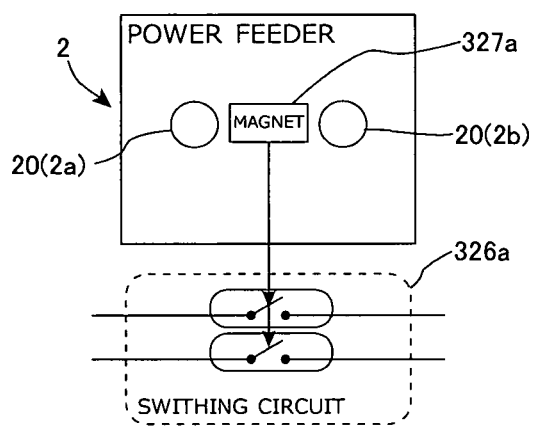
FIGS. 7(a), 7(b) and 7(c) are circuit diagrams showing three specific examples of a switching circuit in the fourth example.

The switch of FIG. 7(a) is a reed switch 326a. In this case, a permanent magnet 327a is provided as the switching control means 327 on the power feeder 2 side, and the reed switch 326a is turned on by the permanent magnet 327a at the time of power feeding (charging), and thus the charging power is supplied from the power feeder 2 to the charging circuit 200, and at the time of the bio-signal measurement, the permanent magnet 327a is separated in distance, whereby the reed switch 326a is turned off.

Figure 7B:
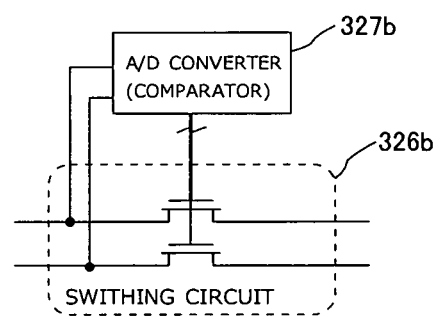

The switch of FIG. 7(b) is composed of a transistor (in this example, FET) 326b as a semiconductor switch, and is turned on and off according to the voltage between the electrodes 10a and 10b. An A/D converter (comparator) 327b which detects the voltage between the electrodes 10a and 10b is used for the switching control means 327.

According to this, the power feeder 2 is connected to the electrodes 10a and 10b for charging, and for example, when the voltage between the electrodes 10a and 10b is 5 V or more, the transistor 326b is turned on. It is turned off at the time of living body measurement.

Figure 7C:
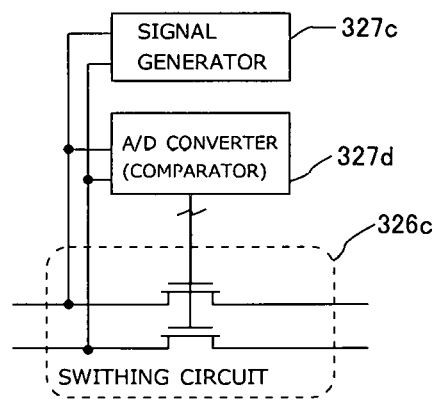

The switch of FIG. 7(c) is also composed of a transistor (FET) 326c as a semiconductor switch, similar to the switch of FIG. 7(b). However. In this case, the switch is turned on and off according to the impedance between the electrodes 10a and 10b.

A signal generator 327c which supplies a measurement signal having a predetermined frequency between the electrodes 10a and 10b, and an A/D converter (comparator) 327d which detects the impedance between the electrodes 10a and 10b at the time of application of the measurement signal are used for the switching control means 327.

According to this, when the power feeder 2 is connected for charging and the impedance between the electrodes 10a and 10b becomes, for example, 100Ω or less, the transistor 326c is turned on. Incidentally, at the time of the bio-signal measurement, the impedance between the electrodes 10a and 10b has a value of, for example, 10 kΩ or more.

Figure 8:
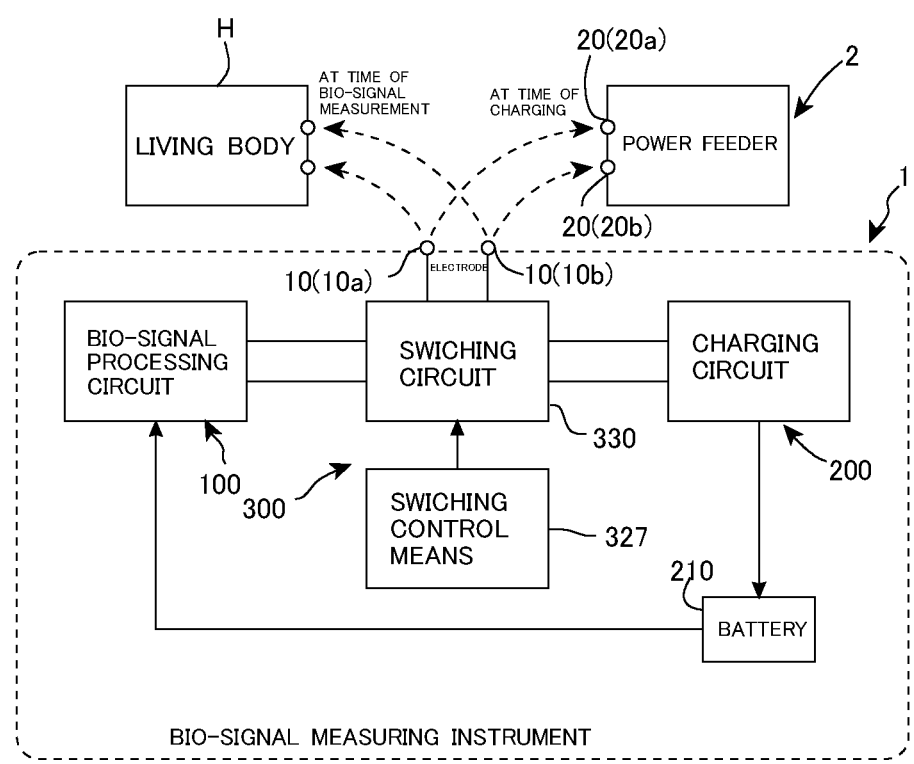
FIG. 8 is a schematic diagram showing a fifth example of the bio-signal and feed power distribution means.

Further, as shown in FIG. 8, a switching circuit 330 may be used as a fifth example of the bio-signal and feed power distribution means 300. According to the switching circuit 330, the electrode 10 is selectively connected to either the bio-signal processing circuit 100 or the charging circuit 200. Three examples thereof are shown in FIGS. 9 (a) to 9 (c).

Figure 9A:
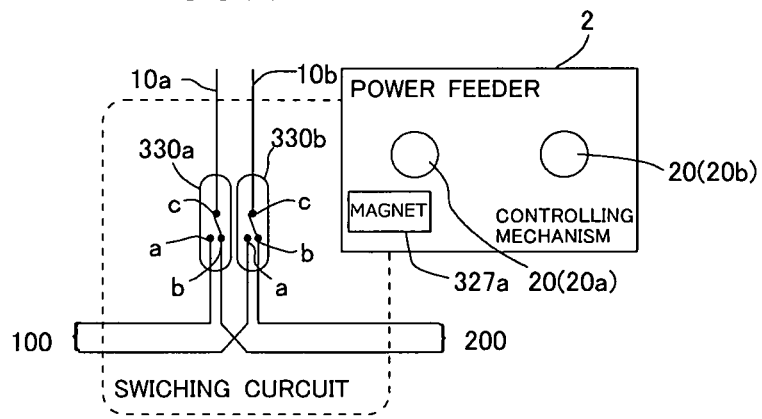
FIGS. 9(a), 9(b) and 9(c) are circuit diagrams showing three specific examples of a switching circuit in the fifth example.

In the example of FIG. 9(a), two reed switches 330a and 330b are used. Each of the reed switches 330a and 330b is a two-contact switching type which is provided with a first contact a and a second contact b which are selectively connected to a common terminal c through a reed piece.

The common terminals c of the reed switches 330a and 330b are respectively connected to the electrodes 10a and 10b side, the first contacts a are connected to the bio-signal processing circuit 100, and the second contacts b are connected to the charging circuit 200. As previously described in FIG. 7(a), the permanent magnet 327a which is provided on the power feeder 2 side is used for the switching control means 327.

According to this, at the time of the power feeding (the time of charging), both the reed switches 330a and 330b are switched to the second contact b side by the permanent magnet 327a, and thus charging power is supplied from the power feeder 2 to the charging circuit 200.

In contrast, at the time of the bio-signal measurement, the permanent magnet 327a is separated in distance, whereby both the reed switches 330a and 330b are switched to the first contact a side, and thus the electrodes 10a and 10b are connected to the bio-signal processing circuit 100.

Figure 9B:
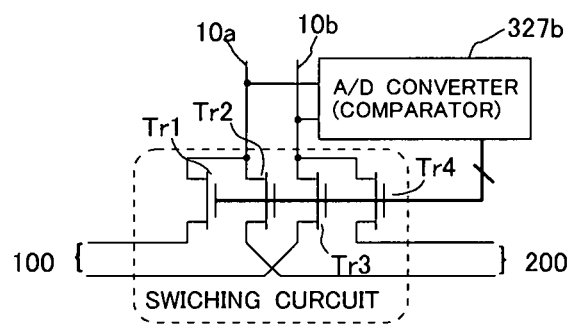

In the example of FIG. 9(b), four transistors (in this example, FETs) Tr1 to Tr4 are used as semiconductor switches.

For example, both the sources of the first transistor Tr1 and the second transistor Tr2 are connected to the side of the electrode 10a on one side, and while the drain of the first transistor Tr1 is connected to the bio-signal processing circuit 100, the drain of the second transistor Tr2 is connected to the charging circuit 200.

For example, both the sources of the third transistor Tr3 and the fourth transistor Tr4 are connected to the side of the electrode 10b on the other side, and while the drain of the third transistor Tr3 is connected to the bio-signal processing circuit 100, the drain of the fourth transistor Tr4 is connected to the charging circuit 200.

As previously described in FIG. 7(b), the A/D converter (comparator) 327b which detects the voltage between the electrodes 10a and 10b may be used for the switching control means 327.

According to this, if the power feeder 2 is connected for charging and, for example, the voltage between the electrodes 10a and 10b is 5 V or more, a predetermined control voltage is applied from the A/D converter 327b to the gates of the second transistor Tr2 and the fourth transistor Tr4, whereby the second transistor Tr2 and the fourth transistor Tr4 become conductive (at this time, both the first transistor Tr1 and the third transistor Tr3 are a non-conduction state), and thus the charging circuit 200 is connected to the electrode 10.

In contrast, at the time of the bio-signal measurement, the voltage between the electrodes 10a and 10b is less than 5 V, and therefore, a predetermined control voltage is applied from the A/D converter 327b to the gates of the first transistor Tr1 and the third transistor Tr1, whereby the first transistor Tr1 and the third transistor Tr1 become conductive (at this time, both the second transistor Tr2 and the fourth transistor Tr4 are in a non-conduction state), and thus the bio-signal processing circuit 100 is connected to the electrode 10.

Figure 9C:
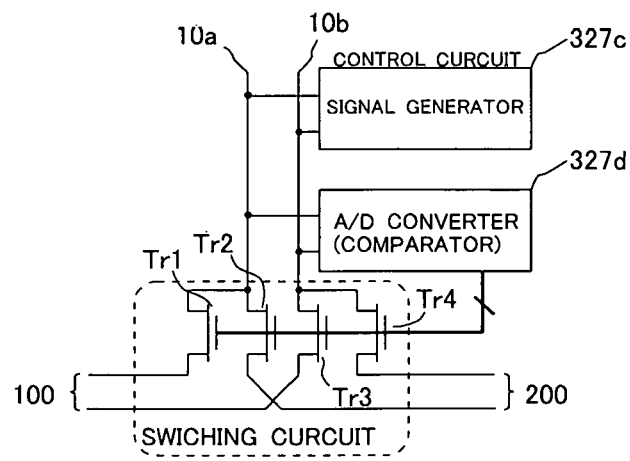

In the example of FIG. 9(c), similar to the example of FIG. 9(b), four transistors (FETs) Tr1 to Tr4 are used as semiconductor switches. Further, similar to the switching control means previously described in FIG. 7(c), the signal generator 327c which supplies a measurement signal having a predetermined frequency between the electrodes 10a and 10b, and the A/D converter (comparator) 327d which detects the impedance between the electrodes 10a and 10b are used for the switching control means 327.

According to this, if the power feeder 2 is connected for charging and the impedance between the electrodes 10a and 10b is, for example, 100Ω or less, a predetermined control voltage is applied from the A/D converter 327d to the gates of the second transistor Tr2 and the fourth transistor Tr4, whereby the second transistor Tr2 and the fourth transistor Tr4 become conductive (at this time, both the first transistor Tr1 and the third transistor Tr3 are is a non-conduction state), and thus the charging circuit 200 is connected to the electrode 10.

In contrast, at the time of the bio-signal measurement, the impedance between the electrodes 10a and 10b is, for example, 10 kΩ or more, and therefore, a predetermined control voltage is applied from the A/D converter 327d to the gates of the first transistor Tr1 and the third transistor Tr3, whereby the first transistor Tr1 and the third transistor Tr3 become conductive (at this time, both the second transistor Tr2 and the fourth transistor Tr4 are in a non-conduction state), and thus the bio-signal processing circuit 100 is connected to the electrode 10.

Figure 10:
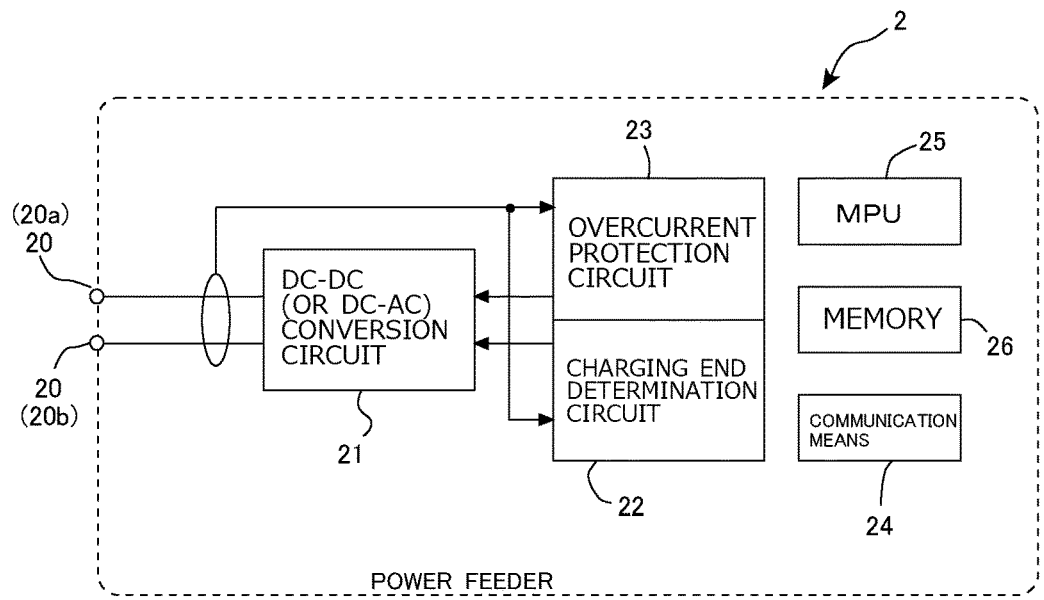
FIG. 10 is a schematic diagram showing a configuration of a power feeder which is included in the bio-signal measuring device according to the present invention.

Next, the power feeder 2 will be described with reference to FIG. 10. The power feeder 2 includes, in addition to a voltage converter 21, a charging end determination circuit 22, and a overcurrent protection circuit 23, communication means 24, an MPU (microprocessor unit) 25 as a control unit, and a memory 26.

The voltage converter 21 may be a DC-DC converter or a DC-AC converter, and converts, for example, a DC voltage (5 V) of a USB into a DC or AC voltage. In the case of the AC power feed, it outputs a differential voltage of, for example, 13.56 MHz and in a range of about 7 to 10 Vp-p on one side. In the case of the DC power feed, it outputs a voltage in a range of 6 to 8 V, for example.

The charging end determination circuit 22 determines charging end from an attenuation state of the feed power at the power feed terminals 20a and 20b. Even in a case where a determination current is reduced, it is possible to cope with it by performing a charging end determination from a current flowing to the power feed terminals 20a and 20b.

In a case where, for example, a capacity of 10 mAh is used as the secondary battery 210 which is mounted on the bio-signal measuring instrument 1, a charging current before the charging end becomes about 1 mA. Although a current value which is used for the charging end determination is a current value smaller than it, the current value can be detected by using a resistor or a current transformer.

The overcurrent protection circuit 23 operates, for example, in a case where the power feed terminals 20a and 20b are short-circuited for some reason, and turns off a power feed switch (not shown) in the voltage converter 21.

Further, the communication means 24 has a function of transmitting biological data or the like stored in the bio-signal measuring instrument 1 to the external equipment (for example, a cloud server or the like), as will be described later, and a function of transferring a command or the like from the external equipment to the bio-signal measuring instrument 1.

The MPU 25 performs advanced processing that cannot be performed in an MCU 121 (refer to FIG. 14) in the bio-signal measuring instrument 1 having a restriction in the power source. The MPU 25 performs, for example, encryption processing or anonymization processing in which an individual cannot be identified, from the viewpoint of personal information protection. The memory 26 temporarily stores the accumulation of past data, case data on the cloud, or the like.

Next, a second embodiment of the bio-signal measuring device will be described with reference to FIG. 11. In the second embodiment, the bio-signal measuring instrument 1 includes an automatic power source switch 110 which is provided in the bio-signal processing circuit 100 to detect the living body and automatically turn on (start) the power source.

The automatic power source switch 110 has a two-input type comparator 111, and the respective one ends of a resistor R1 and a resistor R2 are connected in parallel to an input terminal In1 on one side of the comparator 111. The other end of the resistor R1 is connected to an in-device power source V0, and the other end of the resistor R2 is connected to the ground.

An input terminal In2 on the other side of the comparator 111 is connected to a signal line Lb of the electrode 10b, and a resistor R4 is connected between the input terminal In2 on the other side and the ground. A resistor R3 is connected between a signal line La of the electrode 10a and the in-device power source V0.

When the resistance between the electrodes 10a and 10b is set to be R5, the voltage which is applied to the input terminal In1 on one side is set to be V1, and the voltage which is applied to the input terminal In2 on the other side is set to be V2, V1 and V2 are represented by the following expressions.

$$V1 = V0 \times R2/(R1+R2)$$

$$V2 = V0 \times R4/(R3+R4+R5).$$

The comparator 111 compares V1 with V2, and when V2 is larger than V1, the comparator 111 instructs a power source start IC 112 to start. For example, if R2, R3, and R4 are set to 10 MΩ and R1 is set to 11 mΩ, in a case where the resistance value of the resistance R5 is 1 MΩ or less, V2 becomes larger than V1, and contact with the living body is regarded as being made, whereby the comparator 111 instructs the power source start IC 112 to start and automatically turns on the power source.

It is preferable that the automatic power source switch 110 is disconnected from the power source after the start of the power source. However, if R1 to R4 are set to have high resistance, as described above, even if the automatic power source switch 110 is not disconnected from the power source after the start of the power source, consumption of consumption power can be minimized.

In this example, as described above, R1 to R4 are set to have high resistance, and a consumption current flowing to the comparator 111 and the respective resistors R1 to R4 is always monitored between the electrodes so as to be 1 μA. As an example, a half-life period by a current of 1 μA is about 6 months in a 10 mAh battery, and therefore, there is no influence on the use for several days for collecting biological data.

After the power source start, it is preferable to stop the function of the automatic power source switch. The reason is because there is a case where a DC current flowing to the electrodes 10a and 10b becomes noise in bio-signal detection.

Figure 12:
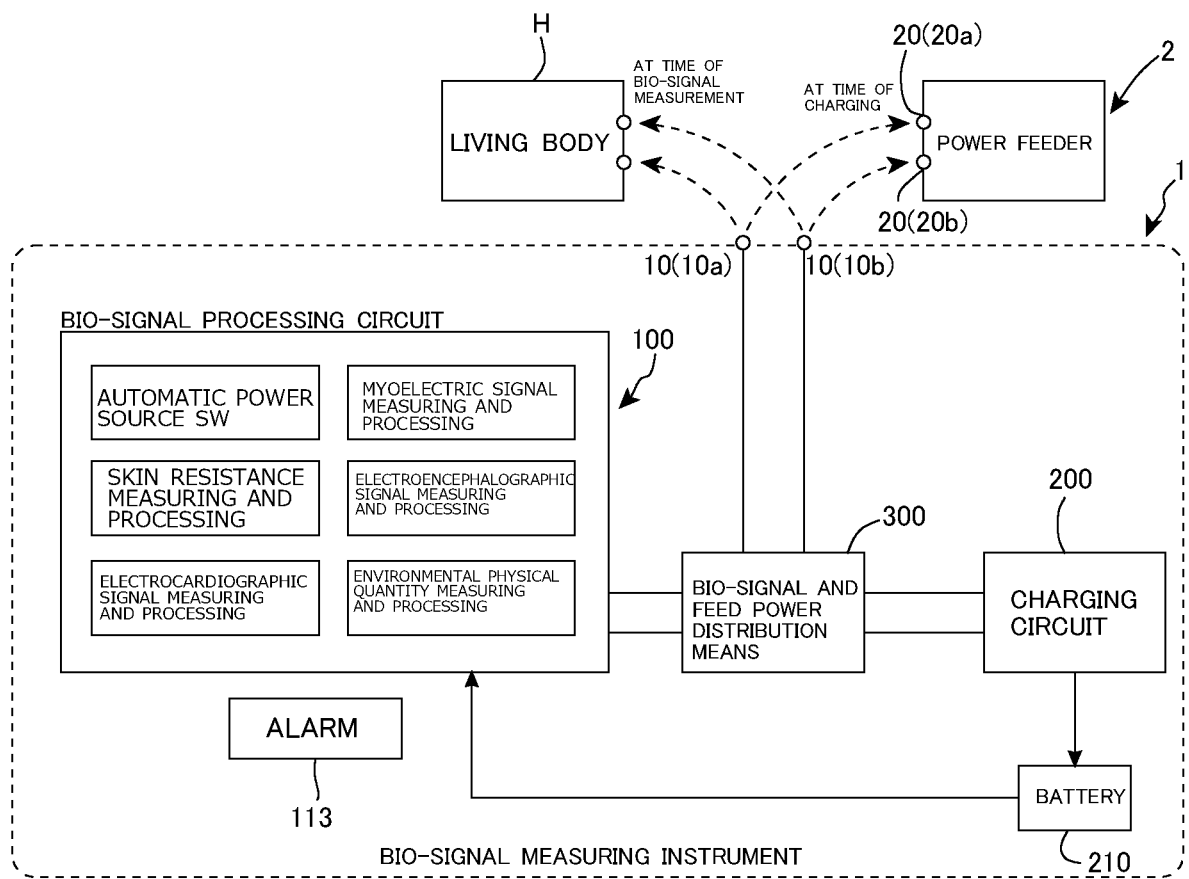
FIG. 12 is a schematic diagram showing a third embodiment of the bio-signal measuring device according to the present invention.

Next, a third embodiment of the bio-signal measuring device will be described with reference to FIG. 12. In the third embodiment, the bio-signal measuring instrument 1 has a mounting state check function.

Figure 11:
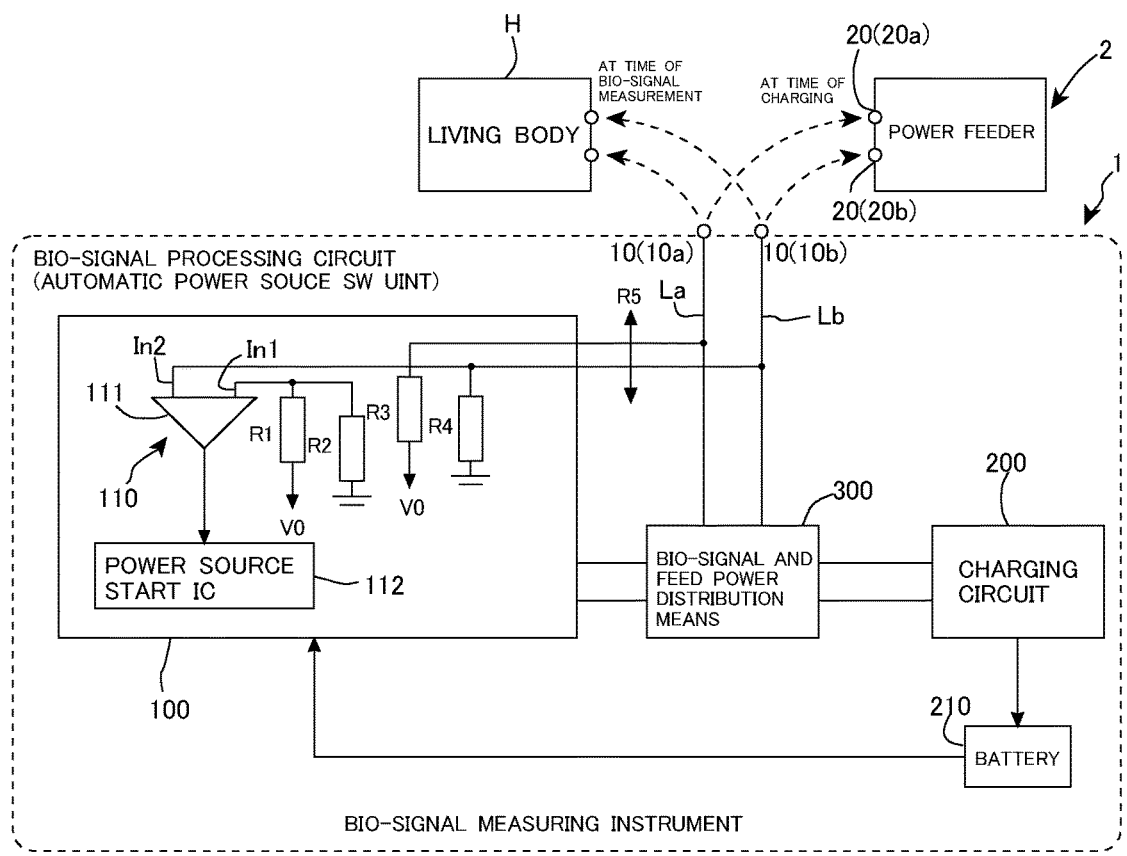
FIG. 11 is a schematic diagram showing a second embodiment of the bio-signal measuring device according to the present invention.

In addition to the automatic power source switch function previously described in FIG. 11, as original measuring and processing functions, a skin resistance measuring and processing unit, an electrocardiographic signal measuring and processing unit, a myoelectric signal measuring and processing unit, an electroencephalographic signal measuring and processing unit, an environmental physical quantity measuring and processing unit, and the like are provided in the bio-signal processing circuit 100 of the bio-signal measuring instrument 1, and from various data of these units, a mounting state of whether or not the bio-signal measuring instrument 1 is correctly mounted to the living body is checked.

As the determination method (algorithm), a determination of whether or not a signal is within the range of a signal level which is expected, a determination by a matching comparison (matched filter) with a template of a waveform which is expected, such as an electrocardiographic waveform, a quantitative comparison with a frequency distribution which is expected by performing frequency analysis, or a signal-to-noise ratio (S/N ratio) which is expected, or the like can be used.

Figure 13:
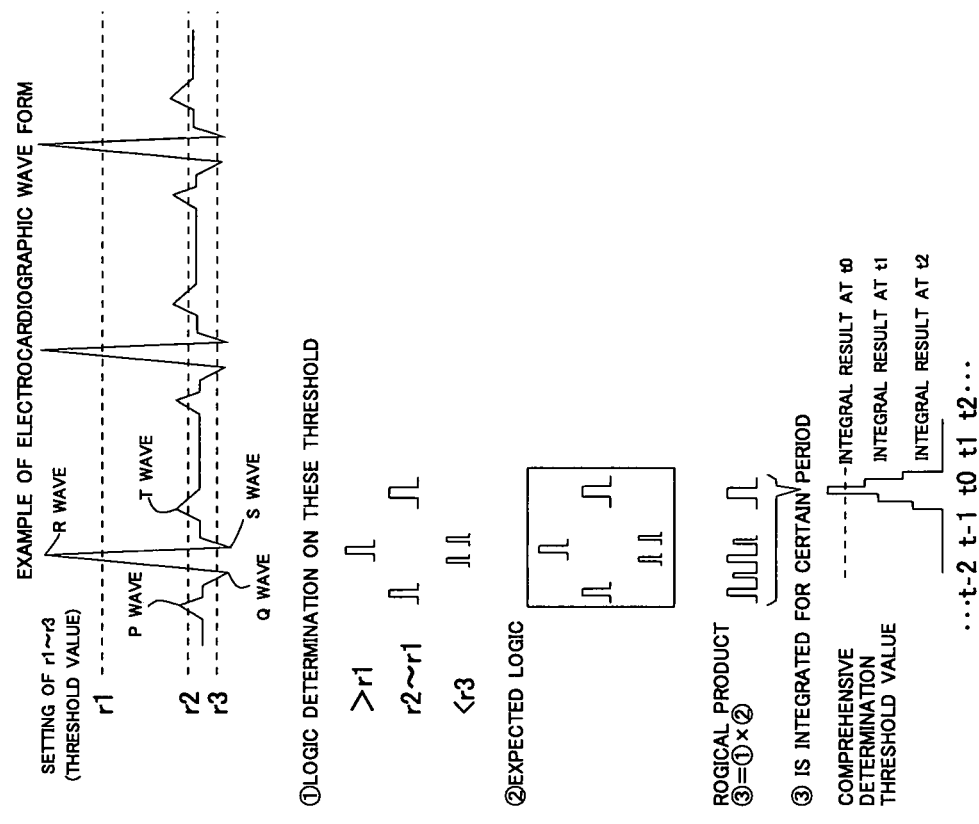
FIGS. 13(*a*) and 13(*b*) are schematic diagrams showing the procedure of a determination which is performed in the third embodiment.
Figure 13:
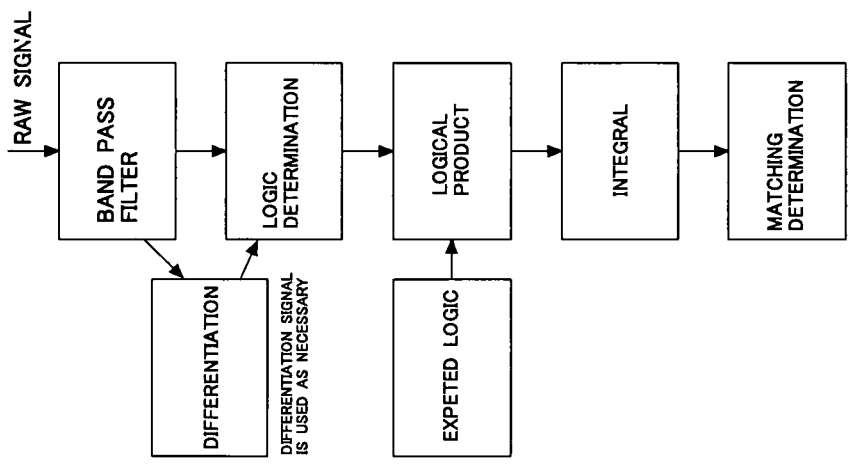

As an example thereof, FIGS. 13(a) and 13(b) show a procedure for determining the mounting state by the matching comparison of the electrocardiographic waveform.

Taking the electrocardiographic waveform as an example, first, as shown in (b-1) of FIG. 13(b), threshold values r1, r2, and r3 (r3<r2<r1) are set with respect to a R wave, a P wave, a T wave, a Q wave, and an S wave, and with respect to the R wave, whether or not it is equal to or more than r1 (r1≤R wave) is determined, and with respect to the P wave and the T wave, whether or not the waves are equal to or more than r2 and less than r1 (r2≤P wave and T wave<r1) is determined, and with respect to the Q wave and the S wave, whether or not the waves are less than r3 (Q wave and S wave<r3) is determined.

Referring to FIG. 13(a), in performing a logic determination on these threshold values, an unnecessary signal component is removed from a raw signal by a band pass filter. At that time, a differential signal may be used as necessary. The logic determination can be performed by a comparator (either digital or analog). The result of the logic determination on the threshold values is shown in (b-2) of FIG. 13(b). However, normalization may be performed with the maximum peak (in this example, the R wave).

Next, a logical produce of expected logic prepared in advance (with a template serving as a criterion for determination, refer to (b-3) of FIG. 13(b)) and the logic determination on the threshold values shown in (b-2) of FIG. 13(b) is taken. An example of the result is shown in (b-4) of FIG. 13(b).

Then, in order to avoid the influence of noise or the like, the logical product is integrated for a certain period, and a threshold value determination of the integral result is performed with a matching determination. As a result, as shown in (b-5) of FIG. 13(b), for example, if the integral result at time t0 exceeds a comprehensive determination threshold value, it is determined that the expected electrocardiographic waveform is detected, that is, it is determined that the bio-signal measuring instrument 1 is correctly mounted to the living body H. If it is not the case, alarm means 113 such as an LED, a vibrator, or a buzzer is operated to notify a wearer of mounting abnormality.

Figure 14:
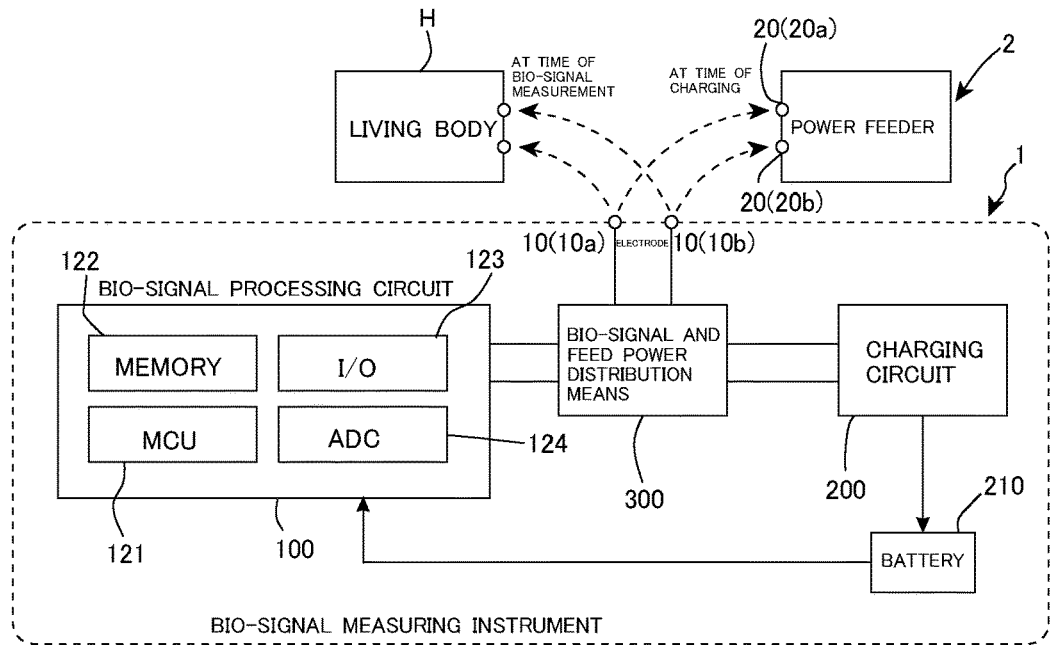
FIG. 14 is a schematic diagram showing a fourth embodiment of the bio-signal measuring device according to the present invention.

Next, a fourth embodiment of the bio-signal measuring device will be described with reference to FIG. 14. In the fourth embodiment, the bio-signal measuring instrument 1 has a communication function with the power feeder 2.

In order to perform communication with the power feeder 2, the MCU (micro controller unit) 121, a memory 122, an I/O interface 123, an ADC (analog-digital conversion circuit) 124, and the like are provided in the bio-signal processing circuit 100 of the bio-signal measuring instrument 1.

The MCU 121 stores the result of processing the bio-signal in the memory 122 and controls the communication with the power feeder 2. As ab example of the processing of the bio-signal, determining a heart rate fluctuation from the electrocardiographic waveform, or determining a movement distance or the amount of exercise from acceleration can be given.

The memory 122 includes a RAM (random access memory) and a ROM (read only memory). The bio-signal data processed in the MCU 121, or the like is stored in the RAM, and a processing program or the like is written in the ROM.

The I/O interface 123 generates a signal for sending data to the power feeder 2. Further, the ADC 124 receives data, a measurement program, or the like from the power feeder 2 and performs replacement of firmware, or the like.

Figure 15:
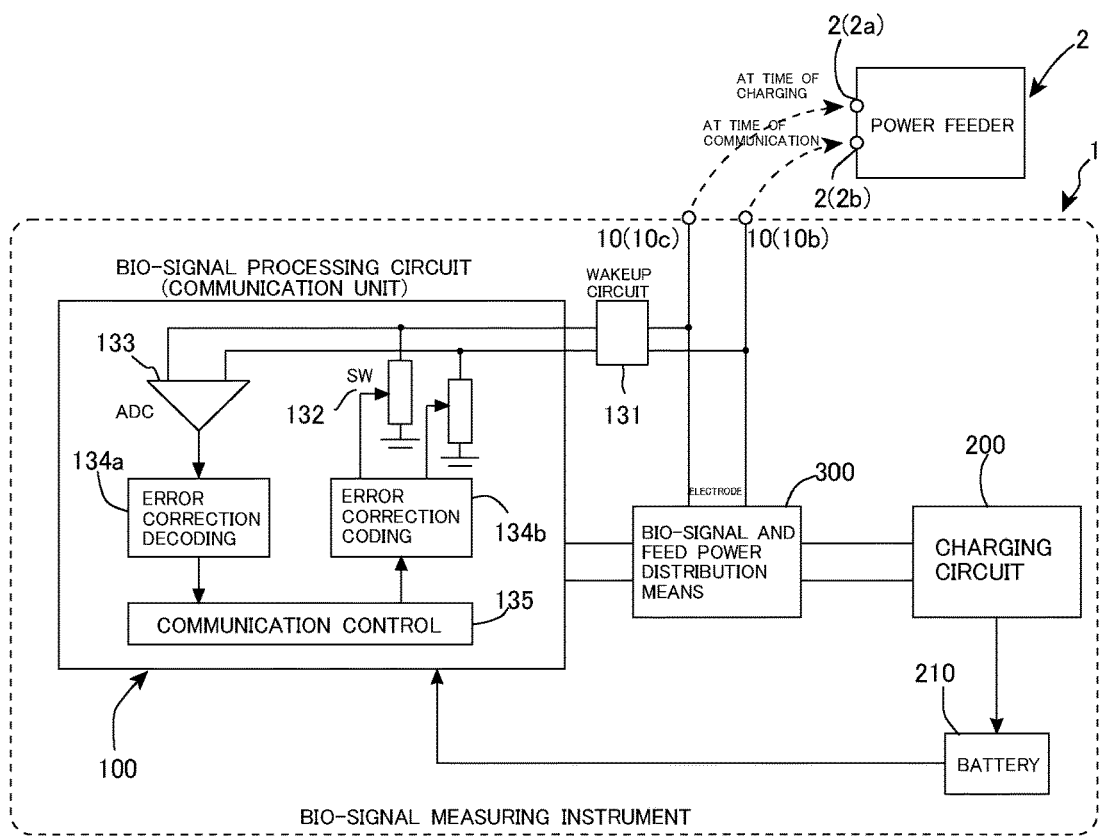
FIG. 15 is a schematic diagram showing a fifth embodiment of the bio-signal measuring device according to the present invention.

As another embodiment (a fifth embodiment of the present invention) of the communication function with the power feeder 2, as shown in FIG. 15, an aspect including a wakeup circuit 131 as connection detection means, a switch (SW) 132 for modulation, an ADC 133, an error correction decoding circuit 134*a*, an error correction coding circuit 134*b*, and a communication control unit 135 is also included in the present invention.

The wakeup circuit 131 detects the feed power (charging power) to determine that this device (the bio-signal measuring instrument 1) is set to the power feeder 2, and causes the communication function to be in an operating state.

The switch 132 for modulation changes the impedance between the differentials in order to modulate the feed power. An external transistor with high withstand voltage can be placed.

The ADC (a comparator is also acceptable) 133 converts the modulation of the feed power into a binary or multiple values. A protective resistor or a protective diode can be placed as necessary.

The an error correction decoding circuit 134*a* and the error correction coding circuit 134*b* reduce the influence of distortion of a transmission path with Reed-Solomon, Viterbi, Turbo, LDPC or the like. The communication control unit 135 generates a transmission and reception timing and controls each part.

FIG. 16 shows an example of data which is transmitted by a communication circuit between the bio-signal measuring instrument 1 and the power feeder 2, and this will be described.

The heart rate fluctuation is obtained from the electrocardiographic waveform by a Floting Unit of the MCU 121 or dedicated HW (hardware), and the heart rate fluctuation is frequency-decomposed into, for example, 16 gradations through a variable band limiting filter. For this, it is preferable to change and decompose the band of an IIR band limiting filter (BPF) little by little.

Recording is performed every certain time, and for example, recording is performed at a rate of once every 10 seconds. The amount of information is 16 frequencies×16 gradations (8 bits)×8640=about 8.6 kB in 24 hours (86400 seconds).

Similarly, the amount of information in 24 hours in a case of frequency-decomposing acceleration is about 10 kB, and the amount of information in 24 hours of a movement distance obtained by integrating acceleration is about 10 kB.

According to the present invention, the power feeder 2 is also referred to as a docking station, and information (biological data or the like) stored in the memory 122 can be transmitted to, for example, a cloud server or the like through the power feeder 2 while charging is performed by connecting the bio-signal measuring instrument 1 to the power feeder 2.

Next, an example of a product form (sensor chip) which is provided to the market of the bio-signal measuring instrument 1 will be described with reference to FIG. 17.

The sensor chip 1 includes two first and second substrates 30 and 40, and a low-bending rigidity part 50 connecting the substrates 30 and 40.

A hard substrate such as a copper-clad laminate substrate is used for each of the substrates 30 and 40, and a flexible wiring board is preferably adopted for the low-bending rigidity part 50. Hereinafter, there is a case where the low-bending rigidity part 50 is referred to as a flexible wiring board.

The surfaces (front surfaces) on one side of the substrates 30 and 40 shown in FIG. 17(*a*) are component mounting surfaces 30*a* and 40*a*, and in this example, the bio-signal processing circuit 100 is mounted on the component mounting surface 30*a* of the first substrate 30, the charging circuit 200 is mounted on the component mounting surface 40*a* of the second substrate 40, and the secondary battery 210 as a power source is mounted on the component mounting surface 40*a*. Since the secondary battery 210 is heavier than the other components, it is preferable to dispose it on the connection portion side. The bio-signal and feed power distribution means 300 may be provided on either the first substrate 30 or the second substrate 40.

The surfaces on the other side of the substrates 30 and 40 shown in FIG. 17(*b*) are back surfaces 30*b* and 40*b*, and while the electrode 10*a* on one side is provided on the back surface 30*b* of the first substrate 30, the electrode 10*b* on the other side is provided on the back surface 40*b* of the second substrate 40. As described above, the electrodes 10*a* and 10*b* are connected to the bio-signal processing circuit 100 and the charging circuit 200 through the bio-signal and feed power distribution means 300.

A length L of the flexible wiring board 50 is preferably as long as possible in order to reduce a force of causing the electrodes 10*a* and 10*b* to be peeled off from the skin. Each side of the substrates 30 and 40 is set to be 30 mm or less, preferably 20 mm or less.

Further, referring to FIG. 17(*c*), the thickness including the electrode 10, the substrates 30 and 40, the bio-signal processing circuit 100, the charging circuit 200, the battery 210, and other members is set to be 10 mm or less, preferably 5 mm or less.

This is for reducing the height from the skin to reduce the force (bending moment) of causing the peel-off. The substrates 30 and 40 does not need to be necessarily a quadrangle and may have curved portions.

Referring to FIG. 18, each of the substrates 30 and 40 is formed of a multilayer build-up substrate which includes an inner layer circuit, and the flexible wiring board 50 is interposed between predetermined inner layers at the time of the build-up. However, in order to enhance the strength, it is preferable to form a through via 51 in the vicinity of each of the facing end portions on the connection side of the substrates 30 and 40. The through via 51 may be filled with plating, a resist, or the like.

With regard to the disposition of the mounted components, as shown in FIG. 18(*b*), disposition may be made such that the bio-signal processing circuit 100 and the battery 210 are disposed on the first substrate 30 on one side and the charging circuit 200 is disposed on the second substrate 40 on the other side. However, preferably, as shown in FIG. 18(*a*), it is favorable if the bio-signal processing circuit 100 is disposed on the first substrate 30 on one side and the charging circuit 200 and the battery 210 are disposed on the second substrate 40 on the other side.

That is, according to the disposition shown in FIG. 18(*a*), the wiring related to the bio-signal processing is arranged on the first substrate 30 side and the wiring of the power source system is arranged on the second substrate 40. Therefore, a circuit pattern which is formed on the flexible wiring board

50 may have a minimum of power source wiring and control wiring, and the flexible wiring board 50 can be made more flexible.

Further, usually, the bio-signal processing circuit 100 has a larger circuit area than the charging circuit 200, and therefore, with the disposition shown in FIG. 18(*a*), the first substrate 30 and the second substrate 40 can have substantially the same size in area.

In this way, the flexible wiring board 50 is disposed substantially at the central portion in a length direction (a right-left direction in FIG. 18) of the sensor chip 1 and the lengths of both the substrates 30 and 40 can be increased. Therefore, the sensor chip 1 can be made difficult to be peeled off from the skin of the living body.

FIG. 19 shows a waterproof cover 60 of the sensor chip 1. FIG. 19(*a*) is a front view of the waterproof cover 60 which covers the sides of the component mounting surfaces 30*a* and 40*a* of the sensor chip 1, FIG. 19(*b*) is a rear view of the waterproof cover 60 which covers the sides of the back surfaces 30*b* and 40*b* of the sensor chip 1, and FIG. 19(*c*) is a sectional view taken along ling A-A of FIG. 19(*b*).

The waterproof cover 60 is made of a low-rigidity material, preferably, silicone rubber, and is formed in the form of a bag which accommodates the sensor chip 1 shown in FIG. 17 in the interior thereof. As shown in FIG. 19(*b*), opening portions 61*a* and 61*b* for exposing the electrodes 10*a* and 10*b* are provided on the back surface side.

Figure 20A:
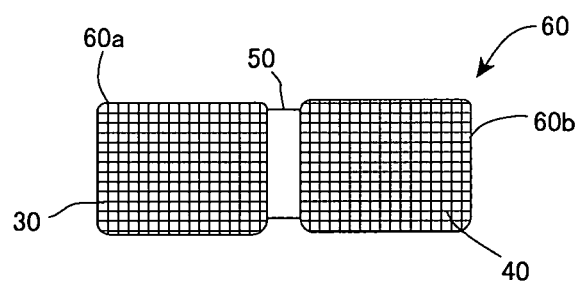
FIGS. 20(*a*) and 20(*b*) are a front view and a rear view showing another example of the waterproof cover.
Figure 20B:
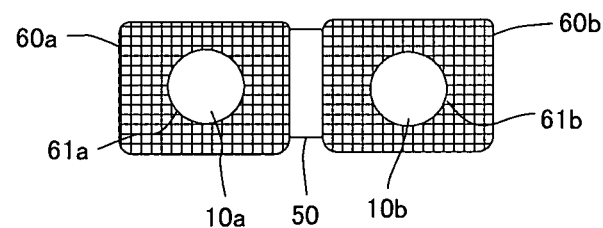

As another example of the waterproof cover 60, as shown in FIG. 20, a configuration is made in which the waterproof cover 60 is divided into two members; a first waterproof cover 60*a* covering the first substrate 30 and a second waterproof cover 60*b* covering the second substrate 40 and the first substrate 30 and the second substrate 40 are individually waterproofed.

As shown in FIG. 20(*b*), the opening portion 61*a* for exposing the electrode 10*a* is provided on the back surface side of the first waterproof cover 60*a*, and the opening portion 61*b* for exposing the electrode 10*b* is provided on the back surface side of the second waterproof cover 60*b*.

According to this, the portion of the flexible wiring board 50 is not covered with a waterproof cover, and therefore, the inherent flexibility of the flexible wiring board 50 is not lost.

The sensor chip 1 may be directly mounted to the skin of the living body. However, preferably, an adhesive tape for mounting 70 shown in FIGS. 21(*a*) and 21(*b*) is used. FIG. 21(*c*) is a schematic diagram showing the electrode surface side of the sensor chip 1, and FIG. 21(*d*) is a schematic diagram showing the power feed terminal side of the power feeder 2.

The adhesive tape for mounting 70 has skin-side electrodes 71*a* and 71*b* made of biocompatible gel or the like and provided at two right and left locations on the skin sticking surface side (pasting surface side) of FIG. 21(*a*). Although not shown, at the time of non-use, the skin-side electrodes 71*a* and 71*b* are covered with release paper.

Connection electrodes 72*a* and 72*b* are provided correspondingly to the skin-side electrodes 71*a* and 71*b* on the surface side (front surface side) shown in FIG. 21(*b*) of the adhesive tape for mounting 70. The connection electrodes 72*a* and 72*b* are made of a magnetic material such as iron and are disposed at an interval equal to the interval between the electrodes 10*a* and 10*b* of the sensor chip 1. Further, the power feed terminals 20*a* and 20*b* of the power feeder 2 are also made of a magnetic material such as iron and are disposed at an interval equal to the interval between the electrodes 10*a* and 10*b* of the sensor chip 1.

In contrast, the electrodes 10*a* and 10*b* of the sensor chip 1 are made of a permanent magnet material, and the sensor chip 1 is selectively held on the adhesive tape for mounting 70 and the power feeder 2 by the magnetic attraction forces of the electrodes 10*a* and 10*b*. FIG. 22 shows a state where the sensor chip 1 is mounted to the adhesive tape for mounting 70.

Next, an example of the procedure of use of the sensor chip 1 will be described with reference to FIGS. 23(*a*) to 23(*f*). First, (a) the release paper is peeled off from the adhesive tape for mounting 70 to expose the skin-side electrodes 71*a* and 71*b*, and (b) the adhesive tape for mounting 70 is stuck to a predetermined site, for example, the chest, of the living body (human body).

Next, (c) the charged sensor chip 1 is mounted to the adhesive tape for mounting 70, as shown in FIG. 22. At this time, the sensor chip 1 is held on the adhesive tape for mounting 70 by the electrodes 10*a* and 10*b* being magnetically attracted to the connection electrodes 72*a* and 72*b*. The sensor chips 1 may be mounted to a plurality of places of the living body.

(d) For example, if the biological data is acquired for several hours to several days and stored in the memory 122, the sensor chip 1 is detached from the adhesive tape for mounting 70, and (e) the sensor chip 1 is set to the power feeder 2. Also at this time, the electrodes 10*a* and 10*b* are magnetically attracted to the power feed terminals 20*a* and 20*b*, whereby the sensor chip 1 is reliably held on the power feeder 2.

If the sensor chip 1 is set to the power feeder 2, the battery 210 of the sensor chip 1 is charged from the power feeder 2. However, in parallel with this, the biological data stored in the memory 122 of the bio-signal processing circuit 100 is transferred to the memory 26 of the power feeder 2.

The transmission of the biological data is performed by the instruction of the MPU 25 of the power feeder 2 and/or the MCU 121 of the sensor chip 1. In this embodiment, the power feeder 2 has a charge lamp 2*a* and a communication lamp 2*b*, the charge lamp 2*a* is lit during the charging, and the communication lamp 2*b* is lit during the data transmission.

After the biological data transmission from the sensor chip 1 to the power feeder 2 is ended, the biological data is deleted from the memory 122 of the sensor chip 1. This data deletion is performed by the instruction of either the MCU 121 of the sensor chip 1 or the MPU 25 of the power feeder 2. (f) In this way, the sensor chip 1 from which the biological data has been deleted and which has been charged is used again to acquire the biological data.

Figure 24:
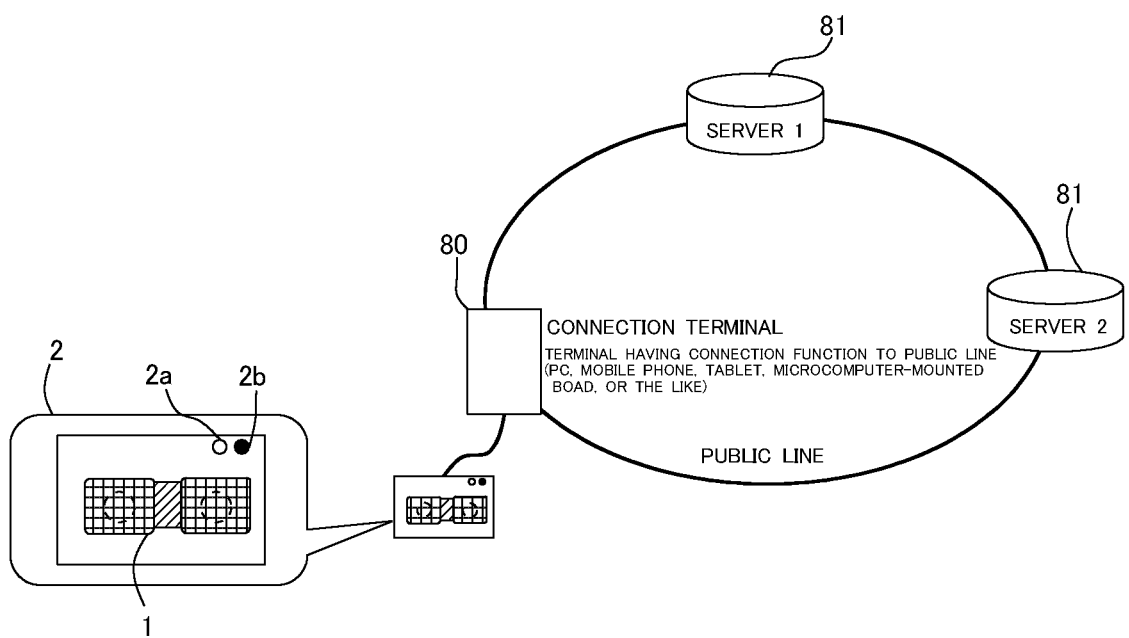
FIG. 24 is a schematic diagram showing a connection state between the bio-signal measuring instrument and external equipment such as a server through a communication line.

As illustrated in FIG. 24, the power feeder 2 is preferably connected to a connection terminal 80 having a connection function to a public line, and transmits the biological data acquired from the sensor chip 1 to a server (cloud server) 81 or the like as the external equipment through, for example, the public line.

The deletion of the biological data from the memory 122 of the sensor chip 1 may be performed after the confirmation of the data transmission to the server 81. Further, as the connection terminal 80, a personal computer, a portable tablet, a microcomputer-mounted board, or the like may be used.

On the server 81 side to which the biological data has been sent from the power feeder 2, physical ability, a stress state, a possibility of falling ill, a state just before falling ill, or the like is determined from the amount of exercise, a pulse change, a heart rate fluctuation, a respiratory rate, a blood pressure change, or the like.

Further, a bio-signal measurement program (for example, a program for measurement of a bio-signal related to a menopausal disorders, a orthostatic dysregulation, arrhythmias, or the like, a program for monitoring and storing specific ST waves in detail, or the like) suitable for the user is written to the sensor chip 1 through the power feeder 2 as necessary.

Also at this time, the communication lamp 2b of the power feeder 2 is lit. However, it does not need to be necessarily performed during the charging. That is, the transmission of the biological data from the sensor chip 1 to the power feeder 2, the transmission of the biological data from the power feeder 2 to the server 81, and program writing from the server 81 to the sensor chip 1 through the power feeder 2 may be performed before or after the charging of the sensor chip 1.

As described above, according to the present invention, an electrode for originally detecting a bio-signal is used as a charging terminal, whereby it is not necessary to provide a dedicated charging terminal such as an SD terminal, and the configuration of the bio-signal measuring instrument is simplified, and thus the size, the weight, and the thickness can be further reduced, and sufficient waterproof measures can be taken.

Further, the power feeder has a communication function (preferably, bidirectional communication) and can transmit the biological data stored in the memory of the bio-signal measuring instrument (sensor chip) to the external equipment through the power feeder even during the charging of the battery, and on the contrary, a predetermined command can be given from the external equipment to the sensor chip through the power feeder or the firmware or the like can be rewritten, and therefore, it is possible to collect effective bio-signals in order to analyze data.

Further, only when the bio-signal measuring instrument (sensor chip) is mounted to the human body, the power source start switch is turned on, so that a power source is supplied from the battery to the bio-signal processing circuit, and otherwise, the power source start switch is turned off. Therefore, battery consumption can be reduced as much as possible.

REFERENCE SIGNS LIST

1: bio-signal measuring instrument (sensor chip)
2: power feeder
10 (10a, 10b): electrode
20 (20a, 20b): power feed terminal
30, 40: substrate
50: low-bending rigidity part (flexible wiring board)
60: waterproof cover
70: adhesive tape for mounting
71a, 71b: skin-side electrode
72a, 72b: connection electrode
100: bio-signal processing circuit
200: charging circuit
300: bio-signal and feed power distribution means

The invention claimed is:

1. A bio-signal measuring device comprising:
a bio-signal measuring instrument which is used in a state of being mounted to a living body,
wherein the bio-signal measuring instrument includes a battery as an internal power source and a charging circuit for the battery, a plurality of electrodes which are brought into contact with a skin surface of a human body at the time of bio-signal measurement and are connected to a predetermined power feeder at the time of charging of the battery, a bio-signal processing circuit which processes bio-signals detected at the electrodes in a predetermined manner, and bio-signal and feed power distribution means,
the bio-signal processing circuit and the charging circuit are switchably connected to the electrodes through the bio-signal and feed power distribution means,
at the time of the bio-signal measurement, the bio-signals detected at the electrodes are supplied to the bio-signal processing circuit through the bio-signal and feed power distribution means, and
at the time of the charging of the battery, feed power which is supplied from the power feeder is supplied to the charging circuit through the bio-signal and feed power distribution means.

2. The bio-signal measuring device according to claim 1, wherein the bio-signal and feed power distribution means includes a signal transfer circuit and a power transfer circuit,
the signal transfer circuit leads the bio-signal to the bio-signal processing circuit at the time of the bio-signal measurement and blocks a flow of the feed power to the bio-signal processing circuit at the time of the charging of the battery, and
the power transfer circuit leads the feed power to the charging circuit at the time of the charging of the battery and blocks a flow of the bio-signal to the charging circuit at the time of the bio-signal measurement.

3. The bio-signal measuring device according to claim 2, wherein in a case where the feed power which is supplied from the power feeder is a direct current, a DC cut filter is used for the signal transfer circuit and a non-linear circuit which includes a diode or a transistor is used for the power transfer circuit.

4. The bio-signal measuring device according to claim 2, wherein in a case where the feed power which is supplied from the power feeder is an alternating current, a low-pass filter is used for the signal transfer circuit and a high-pass filter and a rectifying circuit are used for the power transfer circuit.

5. The bio-signal measuring device according to claim 2, wherein an on/off switch circuit is used for the power transfer circuit.

6. The bio-signal measuring device according to claim 5, wherein a reed switch which is controlled by magnetism of magnetism generating means provided on the power feeder side is used for the switch circuit.

7. The bio-signal measuring device according to claim 5, wherein a semiconductor switch which is turned on and off according to a voltage between the electrodes or impedance between the electrodes is used for the switch circuit.

8. The bio-signal measuring device according to claim 1, wherein a two-contact switching circuit having a first contact which connects the electrode to the bio-signal processing circuit and a second contact which connects the electrode to the charging circuit is used for the bio-signal and feed power distribution means, and the first contact side is closed at the time of the bio-signal measurement and the second contact side is closed at the time of the charging of the battery.

9. The bio-signal measuring device according to claim 8, wherein a reed switch in which the first contact side is closed in a normal state is used for the two-contact switching circuit, and at the time of the charging of the battery, the second contact side is closed by magnetism of magnetism generating means provided on the power feeder side.

10. The bio-signal measuring device according to claim 8, wherein when a voltage between the electrodes is less than a predetermined voltage value or impedance between the electrodes is equal to or more than a predetermined value, the first contact side is closed, and when the voltage between the electrodes is equal to or more than the predetermined voltage value or the impedance between the electrodes is less than the predetermined value, the second contact side is closed.

11. The bio-signal measuring device according to claim 1, further comprising:
a power feeder having power feed terminals which come into contact with the electrodes at the time of the charging of the battery,
wherein the power feeder is provided with a charging end determination circuit which terminates the charging of the battery when a current flowing to the power feed terminals is equal to or less than a predetermined value.

12. The bio-signal measuring device according to claim 11, wherein the bio-signal processing circuit and the power feeder have a communication function of performing communication through the electrodes and the power feed terminals, and at the time of the charging of the battery, bio-signal data processed in the bio-signal processing circuit is transmitted to the power feeder side.

13. The bio-signal measuring device according to claim 12, wherein at the time of the charging of the battery, a predetermined command is provided from the power feeder to the bio-signal processing circuit.

14. The bio-signal measuring device according to claim 1, further comprising:
an automatic power source switch which determines that the electrodes are in contact with the living body, when a resistance value between the electrodes is equal to or less than a predetermined value, and supplies a power source of the battery to the bio-signal processing circuit.

15. The bio-signal measuring device according to claim 1, wherein an electrocardiographic signal measuring and processing unit, an myoelectric signal measuring and processing unit, and an electroencephalographic signal measuring and processing unit are included in the bio-signal processing circuit, and the bio-signal measuring device has a mounting state check function of operating predetermined warning means as poor mounting when any of the measured signals shows an abnormal value.

16. The bio-signal measuring device according to claim 1, further comprising:
a first substrate in which the bio-signal processing circuit is mounted on one surface; and
a second substrate in which the battery and the charging circuit for the battery are mounted on one surface,
wherein the electrode is provided on the other surface side of each of the first substrate and the second substrate, and the first substrate and the second substrate are connected through a low-bending rigidity part having conductive wiring.

17. The bio-signal measuring device according to claim 16, wherein each of the first substrate and the second substrate has a waterproof cover which has an opening portion for exposing the electrode and covers a portion other than the electrode.

18. The bio-signal measuring device according to claim 16, further comprising:
a waterproof cover made of a low-rigidity material, which covers the entirety of the bio-signal measuring instrument including the first substrate, the second substrate, and the low-bending rigidity part.

19. The bio-signal measuring device according to claim 16, further comprising:
an adhesive tape for mounting which is stuck to the living body prior to the bio-signal measurement,
wherein connection electrodes to the living body, which are made of a magnetic material, are disposed at an interval equal to an interval between the electrodes on the adhesive tape for mounting, the electrodes are made of a permanent magnet material, and the bio-signal measuring instrument is mounted to the living body through the adhesive tape for mounting by magnetic attraction of the electrodes to the connection electrodes.

20. The bio-signal measuring device according to claim 1, wherein the bio-signal processing circuit includes a memory to store the bio-signals detected at the electrodes and processed in a predetermined manner,
wherein the power feeder includes communication means for transmitting the bio-signals stored in the memory to a predetermined external equipment.

21. The bio-signal measuring device according to claim 20, wherein the communication means has a bidirectional communication function, and predetermined information which includes a biological data processing program is provided from the external equipment to the bio-signal processing circuit through the communication means.

22. The bio-signal measuring device according to claim 20, wherein the power feeder has power feed terminals which are detachably connected to the electrodes, and communication between the power feeder and the bio-signal measuring instrument is performed through the electrodes and the power feed terminals.

23. The bio-signal measuring device according to claim 22, wherein the bio-signal measuring instrument includes a transmission unit which reads biological data from the memory and transmits the biological data, and connection detection means for outputting a connection detection signal if the power feed terminals are connected to the electrodes, and the transmission unit transmits the biological data to the power feeder if the connection detection signal is output from the connection detection means.

24. The bio-signal measuring device according to claim 23, wherein after transmission of the biological data to the power feeder, the biological data in the memory is deleted.

25. A bio-signal measuring device comprising:
a bio-signal measuring instrument which is used in a state of being mounted to a living body, the bio-signal measuring instrument including a pair of electrodes which is brought into contact with the living body at the time of bio-signal measurement, a bio-signal processing circuit which processes bio-signals detected at the electrodes in a predetermined manner, and a battery which supplies a power source to the bio-signal processing circuit;
a power source start switch which turns on and off the power source which is supplied from the battery to the bio-signal processing circuit; and
a control unit which controls the power source start switch,
wherein the control unit monitors an inter-electrode resistance existing between the electrodes, turns off the power source start switch when the inter-electrode resistance is a value exceeding a predetermined threshold value, and supplies a power source from the battery to the bio-signal processing circuit by turning on the power source start switch when the inter-electrode resistance is equal to or less than the threshold value.

26. The bio-signal measuring device according to claim 25, wherein the control unit has a two-input type comparator, a power source voltage in the device is set to be $V0$, a voltage $V1(=R2/(R1+R2))$ which is obtained by dividing the power source voltage $V0$ with a voltage dividing circuit which includes resistors $R1$ and $R2$ connected between an in-device power source and a ground is applied to an input terminal on one side of the comparator, a voltage $V2$ $(=R4/(R3+R4+R5))$ which is obtained by dividing the power source voltage $V0$ with a voltage dividing circuit which includes a resistor $R3$ connected between the electrode on one side and the in-device power source, a resistor $R4$ connected between the electrode on the other side and the ground, and an inter-electrode resistance $R5$ is applied to an input terminal on the other side of the comparator, the resistors $R2$, $R3$, and $R4$ have the same resistance value $Ra$, the resistor $R1$ has a resistance value $Rb$ higher than the resistance value $Ra$, and the threshold value is defined by $Rb-Ra$.

27. The bio-signal measuring device according to claim 26, wherein the resistors $R1$ to $R4$ are high resistance elements having a consumption current of 1 μA or less.

* * * * *